United States Patent
Yardibi et al.

(10) Patent No.: US 12,161,421 B2
(45) Date of Patent: Dec. 10, 2024

(54) IMAGING DURING A MEDICAL PROCEDURE

(71) Applicant: Medos International Sarl, Le Locle (CH)

(72) Inventors: Tarik Yardibi, Wayland, MA (US); Raymond Parfett, Loveland, OH (US); R. Patrick Courtis, Dorchester, MA (US); Emir Osmanagic, Norwell, MA (US)

(73) Assignee: Medos International Sarl, Le Locle (CH)

( * ) Notice: Subject to any disclaimer, the term of this patent is extended or adjusted under 35 U.S.C. 154(b) by 472 days.

(21) Appl. No.: 17/390,115

(22) Filed: Jul. 30, 2021

(65) Prior Publication Data

US 2023/0034101 A1     Feb. 2, 2023

(51) Int. Cl.
*A61B 34/10*     (2016.01)
*A61B 34/00*     (2016.01)
(Continued)

(52) U.S. Cl.
CPC .............. *A61B 34/10* (2016.02); *A61B 34/25* (2016.02); *A61B 90/37* (2016.02); *G06T 7/0012* (2013.01);
(Continued)

(58) Field of Classification Search
CPC ......... A61B 34/10; A61B 34/25; A61B 90/37; A61B 2034/102; A61B 2034/105; A61B 2034/107; A61B 2090/3762; A61B 5/004; A61B 5/055; A61B 6/032; A61B 6/04; A61B 2505/05; A61B 5/4893; A61B 5/7264; A61B 2034/2055; A61B 2090/365; A61B 2090/3764; A61B 2090/378;
(Continued)

(56) References Cited

U.S. PATENT DOCUMENTS 8,394,129 B2 *   3/2013   Morgenstern Lopez ..................... A61B 17/8858 606/279
8,518,087 B2 *   8/2013   Lopez ................... A61F 2/4455 606/279

(Continued)

FOREIGN PATENT DOCUMENTS

EP           3608870 A1    2/2020
WO     2020/023740 A1    1/2020

OTHER PUBLICATIONS

Fan Guoxin et al: "Deep learning-based lumbosacral reconstruction for difficulty prediction of percutaneous endoscopic transforaminal discectomy at L5/S1 level: A retrospective cohort study", International Journal of Surgery, Surgical Associates, London, GB, vol. 82, Sep. 1, 2020 (Sep. 1, 2020), pp. 162-169.

(Continued)

*Primary Examiner* — Santiago Garcia
(74) *Attorney, Agent, or Firm* — BakerHostetler

(57) ABSTRACT

A system may be configured to facilitate a medical procedure. Some embodiments may: acquire a scan corresponding to a region of interest (ROI); capture an image of a patient in real-time; identify, via a trained machine learning (ML) model using the acquired scan and the captured image, a Kambin's triangle; and overlay, on the captured image, a representation of the identified Kambin's triangle.

19 Claims, 20 Drawing Sheets

(51) Int. Cl.
  *A61B 90/00* (2016.01)
  *G06T 7/00* (2017.01)
  *G06T 7/11* (2017.01)
(52) U.S. Cl.
  CPC ........... *G06T 7/11* (2017.01); *A61B 2034/102* (2016.02); *A61B 2034/105* (2016.02); *A61B 2034/107* (2016.02); *A61B 2090/3762* (2016.02); *G06T 2207/10081* (2013.01); *G06T 2207/20081* (2013.01); *G06T 2207/20084* (2013.01); *G06T 2207/20104* (2013.01); *G06T 2207/30012* (2013.01)
(58) Field of Classification Search
  CPC ........ A61B 2090/3983; A61B 2576/02; G06T 7/0012; G06T 7/11; G06T 2207/10081; G06T 2207/20081; G06T 2207/20084; G06T 2207/20104; G06T 2207/30012; G06N 3/045; G06N 3/08; G16H 20/40; G16H 50/20; G16H 30/40
  See application file for complete search history.

(56) References Cited

U.S. PATENT DOCUMENTS

| | | | | |
|---|---|---|---|---|
| 10,743,915 | B2* | 8/2020 | Lopez | A61B 17/885 |
| 11,278,353 | B2* | 3/2022 | Sela | G16Z 99/00 |
| 2012/0232658 | A1* | 9/2012 | Morgenstern Lopez | A61F 2/447 606/90 |
| 2017/0148213 | A1* | 5/2017 | Thomas | A61B 34/20 |
| 2017/0265943 | A1* | 9/2017 | Sela | A61B 34/20 |
| 2018/0042735 | A1* | 2/2018 | Schell | A61F 2/4611 |
| 2018/0092559 | A1* | 4/2018 | Wybo | A61B 5/4893 |
| 2018/0103983 | A1* | 4/2018 | Lopez | A61B 5/24 |
| 2019/0008554 | A1* | 1/2019 | Lopez | A61F 2/4611 |
| 2019/0262084 | A1* | 8/2019 | Roh | G16H 30/40 |
| 2022/0148454 | A1* | 5/2022 | Jaramaz | A61B 34/25 |
| 2022/0167868 | A1* | 6/2022 | Sela | A61B 34/20 |
| 2022/0249174 | A1* | 8/2022 | Shinohara | A61B 90/37 |
| 2022/0351410 | A1 | 11/2022 | Siemionow et al. | |
| 2022/0399117 | A1* | 12/2022 | Leuthardt | G16H 50/20 |

OTHER PUBLICATIONS

Yamada Katsuhisa et al: "Morphological analysis of Kambin's triangle using 3D CT/MRI fusion imaging of lumbar nerve root created automatically with artificial intelligence", European Spine Journal, Springer Berlin Heidelberg, Berlin/Heidelberg, vol. 30, No. 8, Jul. 3, 2021 (Jul. 3, 2021), pp. 2191-2199.

Cicek et al., 3D U-Net: Learning Dense Volumetric Segmentation from Sparse Annotation, CoRR 2016.

Epstein, More nerve root injuries occur with minimally invasive lumbar surgery, especially extreme lateral interbody fusion: A review, Surg Neurol Int. Jan. 25, 2016;7 (Suppl 3):S83-95.

Ikuta et al., Surgical complications of microendoscopic procedures for lumbar spinal stenosis, Minim Invasive Neurosurg. 2007;50:145-149.

Parikh et al., Operative results and learning curve: microscope-assisted tubular microsurgery for 1- and 2-level discectomies and laminectomies, Neurosurg Focus, 2008;25:E14.

Podichetty et al., Complications associated with minimally invasive decompression for lumbar spinal stenosis, J Spinal Disord Tech., 2006;19:161-166.

Thirumala, Perioperative neurologic complications during spinal fusion surgery: incidence and trends, The Spine Journal vol. 17, Issue 11, Nov. 2017, pp. 1611-1624.

Wu et al., Microendoscopic discectomy for lumbar disc herniation: surgical technique and outcome in 873 consecutive cases, Spine (Phila Pa 1976) 2006;31:2689-2694.

* cited by examiner

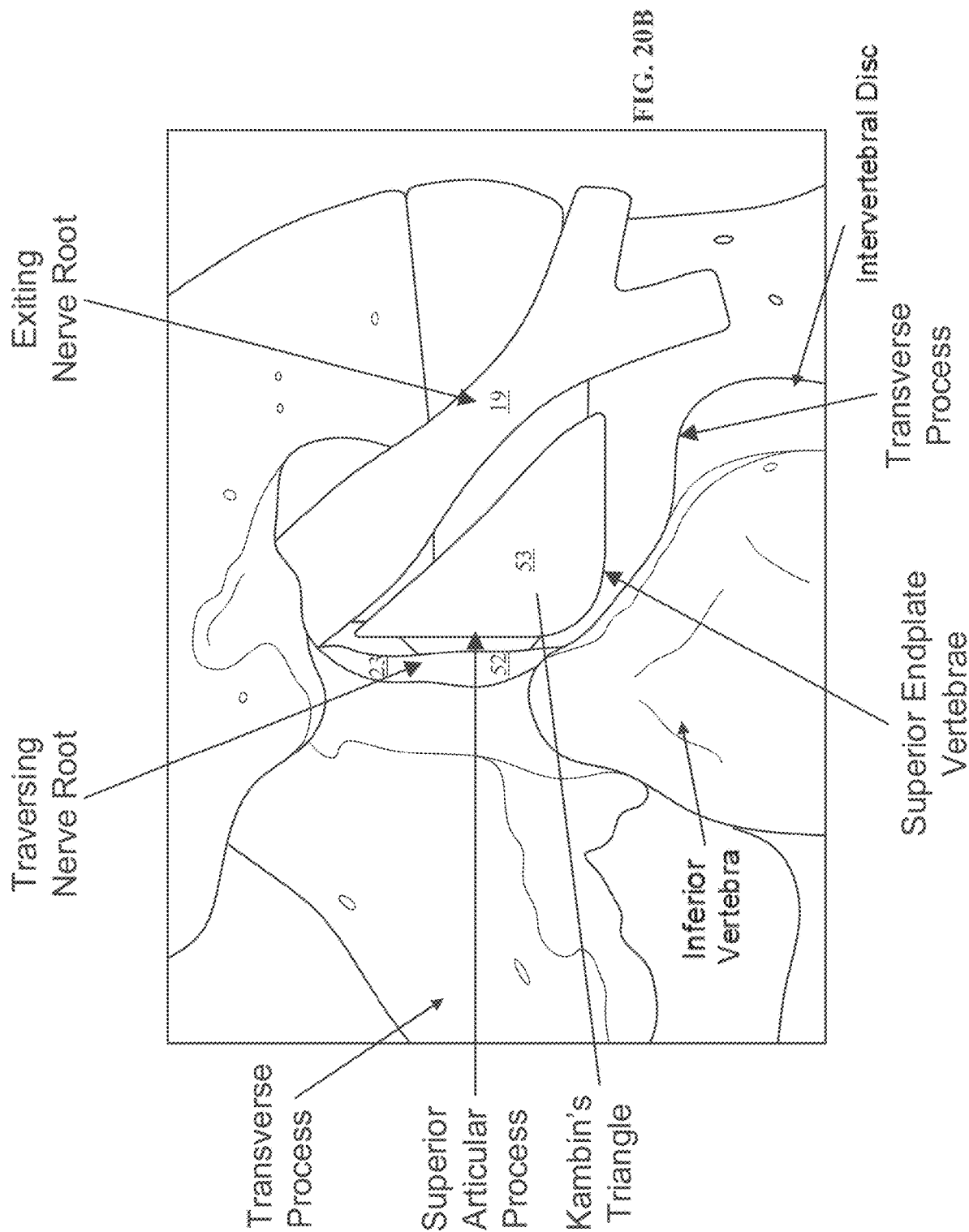

IMAGING DURING A MEDICAL PROCEDURE

TECHNICAL FIELD

The present disclosure is generally related to systems and methods for reducing neurological complications associated with surgery by identifying and modeling a predicted location of neurological structures. The present disclosure is also related to the creation, use, and application of machine-learning networks and models to predictively locate an anatomical structure based on learned anatomical associations.

The present disclosure further relates to systems and methods for predicting presence of different aspects within the body to then identify a target and/or determine a path thereto.

BACKGROUND

Perioperative neurological injury is a known complication associated with elective spinal surgery. Neurological injury can result when contact occurs with neurological structures during a surgical procedure. Some examples of perioperative neurological complications that may result from spinal surgery include vascular injury, durotomy, nerve root injury, and direct mechanical compression of the spinal cord or nerve roots during vertebral column instrumentation. Wide variation in patient anatomy can make it difficult to accurately predict or identify a location of neurological structures in a particular patient's spinal region.

According to data from the National Institute of Science, the incidence of perioperative neurological injuries resulting from elective spine surgery increased 54.4%, from 0.68% to 1%, between 1999 and 2011. Additionally, perioperative neurological complications in elective spine surgery were associated with longer hospital stays (9.68 days vs. 2.59 days), higher total charges ($110,326.23 vs. $48,695.93), and increased in-hospital mortality (2.84% vs. 0.13%).

While minimally invasive spine surgery (MISS) has many known benefits, multi-study analysis of patient outcome data for lumbar spine surgery indicate that MISS has a significantly higher rate of nerve root injury (2%-23.8%) as compared to traditional 'open' surgical techniques (0%-2%). With MISS procedures, accessing the spine or a target surgical region often involves navigating a surgical instrument through patient anatomy including muscles, fatty tissue, and neurological structures. Current intra-operative imaging devices do not adequately show neurological structures in an operating region. For example, computed tomography (CT) and cone beam computed tomography (CBCT) imaging technology is often used intra-operatively to visualize musculoskeletal structures in an operating region of a patient's anatomy. CT and CBCT images, however, do not show neurological structures. Furthermore, the current practice is to use CT imaging for preoperative planning of a surgical approach. Since neurological structures are not visible in CT image volumes, a surgical approach cannot be optimized to avoid or reduce contact with neurological structures. While magnetic resonance imaging (MRI) imaging shows both musculoskeletal and neurological structures of a scanned patient anatomy, MRI imaging is typically used only to diagnose a patient and not for pre-operative surgical planning or intra-operative use.

Although the incidence of perioperative neurological injury in MISS procedures is greater than traditional open surgical techniques, MISS remains an attractive treatment option for spinal disorders requiring surgery. Benefits of MISS, as compared to open surgery, include lower recovery time, less post-operative pain, and smaller incisions.

Accordingly, there is a need for systems and methods for reducing the incidence of neurological complications in spinal surgery, and, in particular, for reducing the incidence of neurological complications in minimally invasive spinal surgery.

During MISS surgery, it is difficult to identify anatomical structures, even for experienced practitioners, and therefore multiple technologies are often utilized. CT non-invasive scans comprise of X-rays to produce detailed, three-dimensional (3D) images of a region of interest (ROI) of a body or patient (e.g., person or animal). MRI comprises non-invasive use of magnets to create a strong magnetic field and pulses to create 3D images of the target or ROI. Endoscopes provide visual information in real-time on the surgery site. CT and MRI scans can be overlaid on a camera's image and visualizations may be performed via augmented reality (AR) or virtual reality (VR).

SUMMARY

Systems and methods are disclosed for identifying where to insert a medical instrument (e.g., during a medical procedure, such as minimally invasive transforaminal interbody lumbar fusion (TLIF) surgery), without thereafter contacting with a nerve or bone when advancing the instrument therein. Accordingly, one or more aspects of the present disclosure relate to a method for: acquiring a scan corresponding to a ROI; capturing an image of a patient in real-time; identifying, via a trained machine learning model using the acquired scan and the captured image, a Kambin's triangle; and overlaying, on the captured image, a representation of the identified triangle.

The method is implemented by a system comprising one or more hardware processors configured by machine-readable instructions and/or other components. The system comprises the one or more processors and other components or media, e.g., upon which machine-readable instructions may be executed. Implementations of any of the described techniques and architectures may include a method or process, an apparatus, a device, a machine, a system, or instructions stored on computer-readable storage device(s).

Any of the features or variations described above can be applied to any particular aspect or embodiment of the present disclosure in a number of different combinations. The absence of explicit recitation of any particular combination is due solely to the avoidance of repetition.

BRIEF DESCRIPTION OF THE DRAWINGS

The details of particular implementations are set forth in the accompanying drawings and description below. Like reference numerals may refer to like elements throughout the specification. Other features will be apparent from the following description, including the drawings and claims. The drawings, though, are for the purposes of illustration and description only and are not intended as a definition of the limits of the disclosure.

FIGS. 20A-20B are schematic views of an identified Kambin's triangle, in accordance with one or more embodiments.

DETAILED DESCRIPTION

Figure 1:
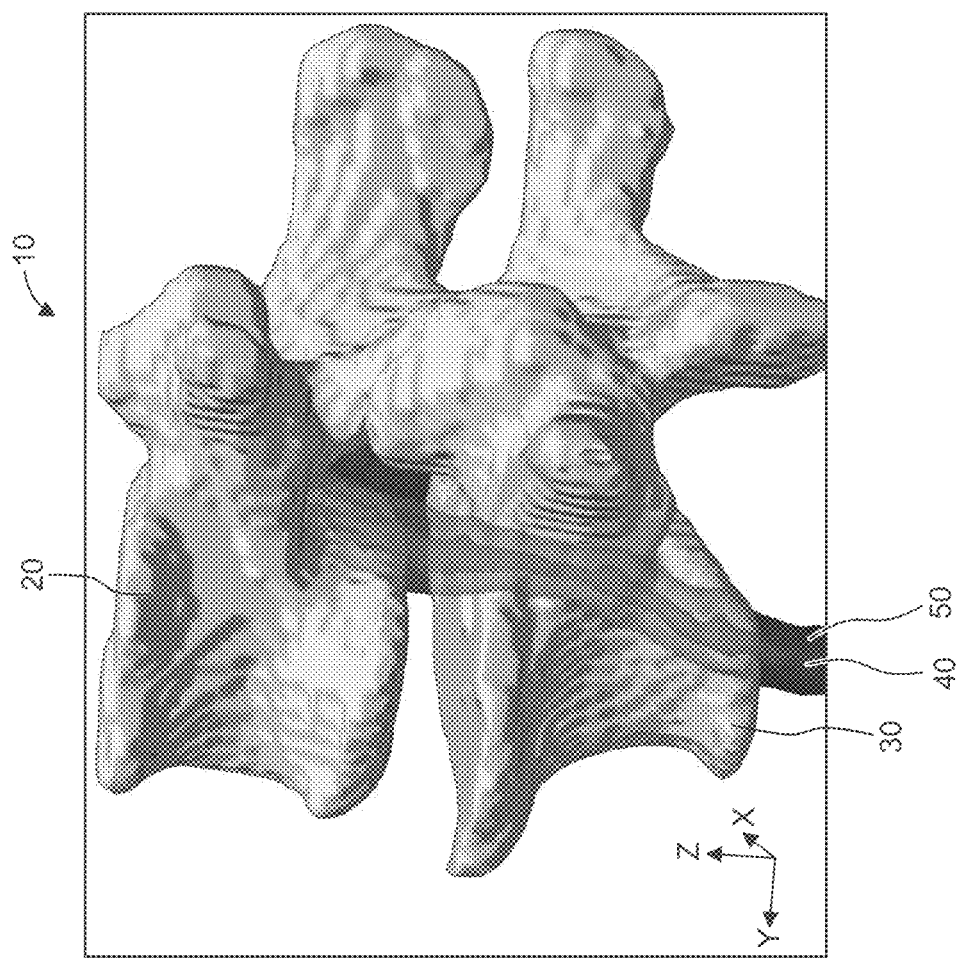
FIG. 1 shows an exemplary 3D model output of an image analysis tool of the present invention.

As used throughout this application, the word "may" is used in a permissive sense (i.e., meaning having the potential to), rather than the mandatory sense (i.e., meaning must). The words "include," "including," and "includes" and the like mean including, but not limited to. As used herein, the singular form of "a," "an," and "the" include plural references unless the context clearly dictates otherwise. As employed herein, the term "number" shall mean one or an integer greater than one (i.e., a plurality).

As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

These drawings may not be drawn to scale and may not precisely reflect structure or performance characteristics of any given embodiment, and should not be interpreted as defining or limiting the range of values or properties encompassed by example embodiments.

Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Still further, sizes and shapes of the devices, and the components thereof, can depend at least on the anatomy of the subject in which the devices will be used, the size and shape of components with which the devices will be used, and the methods and procedures in which the devices will be used.

While the illustrated embodiments and accompanying description make particular reference to application in a spinal surgery procedure, and, in particular, to minimally invasive spinal surgery, the devices, systems, and methods described herein are not limited to these applications.

Some background information on imaging and neural networks will now be provided. As discussed above, there is a need in the medical field to reduce the incidence of neurological complications associated with elective spinal surgery. In current practice MRI imaging can visualize both musculoskeletal and neurological structures or tissues in a scanned region of a patient's anatomy. However, MRI imaging is not preferred for use in pre-operative surgical planning or intra-operative planning or feedback. CT imaging and CBCT imaging can be used to show musculoskeletal structures in a scanned region of a patient's anatomy. Neurological structures, however, are not visible in CT or CBCT image volumes. CT or CBCT imaging is commonly used by surgeons in pre-operative surgical planning and/or intra-operative surgical navigation, planning, or analysis. In particular, for a minimally invasive spinal surgical procedure CT or CBCT image volumes can be used pre-operatively to plan a surgical access approach for a surgical instrument to follow to access a target spinal region. In some surgical procedures using a computer assisted navigation environment, CT or CBCT imaging can be used intra-operatively to display a surgical region of a patient's anatomy. The CT or CBCT imaging can be updated if a patient position is adjusted during the procedure.

For MRI and CT or CBCT imaging, a resulting image volume can be annotated, labeled, or segmented to identify different anatomical structures. The process of identifying structures in an image volume can be referred to as annotating, labeling, or segmenting the image volume and these terms are used interchangeably throughout the disclosure herein. Alternatively, a resulting image volume can remain as an unsegmented volume. In the case of an unsegmented volume, the resulting image volume does not include data differentiating structures visible in the image volume from one another.

Recent developments in machine-learning algorithms include the development of a U-Net which is a (deep) convolutional neural network (CNN) for application in biomedical image segmentation. In general, a CNN is a deep neural network having multiple layers between an input layer and an output layer. A CNN can be trained to decompose an input image, identify trends that exist across all samples of input imagery, and classify unlabeled input imagery using the identified trends without requiring human input. In this manner, a CNN can learn image filters which, in traditional algorithms, were hand engineered.

In a recent work, a known U-net architecture has been built upon to create a U-net based deep network that learns to generate dense volumetric segmentations from only a few annotated 2D slices. The semi-automated deep network can densify segmentations that are present in the annotated 2D input slices. In a fully automated setup, a representative sparsely annotated training data set exists and can be input to train the neural network to densely segment new volumetric images. In both cases, the deep neural network uses a U-net architecture to generate a dense segmentation of an anatomical structure that is shown, but not densely segmented, in an input image.

Figure 17:
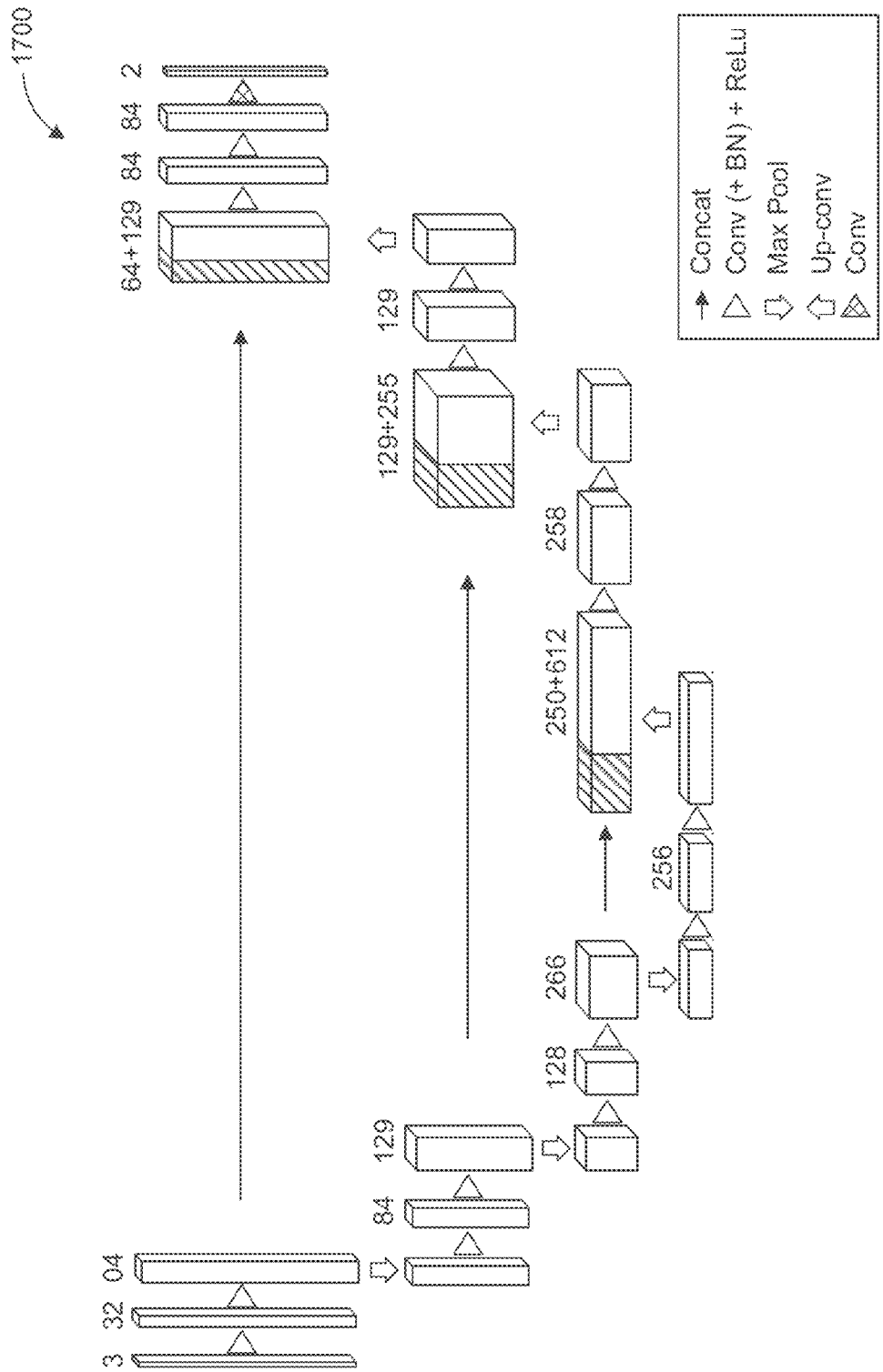
FIG. 17 shows a prior art U-net architecture.

FIG. 17 shows an illustration of a known U-net architecture 1700, which consists of a contracting encoder part to analyze the whole image and a successive expanding decoder part to produce a full-resolution segmentation. The u-net architecture of FIG. 17 takes 3D volumes as input and processes them with corresponding 3D operations, in particular, 3D convolutions, 3D max pooling, and 3D up-convolutional layers. The u-net architecture has an analysis and a synthesis path each with four resolution steps. In the analysis path, each layer contains two 3×3×3 convolutions each followed by a rectified linear unit (ReLu), and then a 2×2×2 max pooling with strides of two in each dimension. In the synthesis path, each layer consists of an upconvolution of 2×2×2 by strides of two in each dimension, followed by two 3×3×3 convolutions each followed by a ReLu. Shortcut connections from layers of equal resolution in the analysis path provide the essential high-resolution features to the synthesis path. In the last layer a 1×1×1 convolution reduces the number of output channels to the number of labels, which in the case of FIG. 17 is 3. The architecture shown in FIG. 17 has 19,069,955 parameters in total. Bottlenecks are avoided by doubling the number of channels already before max pooling. The same is done in the synthesis path.

With continued reference to FIG. 17, the input to the network is a 132×132×116 voxel tile of the image with 3 channels. The output in the final layer is 44×44×28 voxels in x, y, and z directions respectively. With a voxel size of 1.76×1.75×2.04 µm3, the approximate receptive field becomes 155×155×180 µm3 for each voxel in the predicted segmentation. As such, each output voxel has enough context to learn efficiently. A batch normalization is introduced before each ReLu. Each batch is normalized during training with its mean and standard deviation and global statistics updated using these values. This is followed by a layer to learn scale and bias explicitly. The u-net architecture includes a weighted softmax loss function. The weight of unlabeled pixels can be set to zero, making it possible to learn from only the labeled pixels and generalize to a whole volume.

The systems and methods disclosed herein can include an image analysis tool that expands on a u-net architecture to effectively and predictively identify, label, model, and visualize anatomical structures from an unlabeled input volume.

Generally, a disclosure of predictive modelling and visualization of neural anatomy for spinal surgery will now be presented. The present invention is generally directed to methods, systems, and devices to predictively locate, model, and visualize neurological tissue from an unsegmented, or unlabeled, image volume of a patient's anatomy. The methods, systems, and devices described herein are especially well-suited for use in association with a spinal surgery procedure and, in particular, for use in a minimally invasive spinal surgery procedure. An image analysis tool of the present invention can be trained to predictively locate, model, and visualize neurological structures near a patient's spine from an unlabeled image volume of the patient's spinal region. The image analysis tool of the present invention can be configured as a machine-learning system. In one embodiment, the image analysis tool can include multiple convolution neural networks. In one embodiment, the image analysis tool can include a first convolution neural network that is configured as a trained predictive model and a second convolution neural network that uses the first convolution neural network as a ground truth pixel label classification. A first convolution neural network and a second convolution neural network of the present invention can also be referred to as a first U-Net and a second U-Net, respectively.

An image analysis tool of the present invention can receive as an input an unlabeled CT or CBCT scan volume of a spinal region, and can use a trained neural network to predict a location of and identify at least one neurological structure associated with the scanned spinal region. The image analysis tool can output, with some degree of confidence, a segmented or labeled image of the scanned spinal region. In one embodiment, the image analysis tool can output a 3D model of labeled neurological structures near the spine from an unsegmented patient scan. The image analysis tool output can provide an initial patient-specific 'nerve road map' for optimizing a surgical approach to avoid contact with neurological structures based on patient-specific anatomy. The image analysis tool can rely on a deep-learning based covariation model of neurological and musculoskeletal anatomy to make associations to predictively model and identify neural tissue with some level of confidence. In accordance with the present invention, additional patient imaging, such as imaging using MRI or ultrasound, is not required to identify the location of neural tissue near a patient's spine.

In one embodiment, an image analysis tool of the present invention can be used as part of a computer assisted navigation environment that can include, for example, intra-operative CBCT and tool tracking. An image analysis tool of the present invention can be incorporated or used in association with any known computer assisted navigation environment. Incorporating the image analysis tool of the present invention with a computer assisted navigation environment can allow for intra-operative adjusting and updating of predictive modeling and visualization of neurological structures and/or patient-specific surgical plans. A computer assisted navigation environment can receive intra-operative feedback with respect to a surgical procedure being performed. For example, intra-operative feedback can include information regarding a position of a patient, a neurological structure, or a surgical instrument and can be used in conjunction with a model of the neurological structures generated by the present invention to reduce unwanted contact with neurological structures. The predictive modeling and visualization of the neurological structures generated by an image analysis tool can be verified intra-operatively through feedback from neural monitoring probes, arthroscopic cameras, etc.

A patient-specific surgical plan generated in the present invention can also be used as part of a computer assisted navigation or a robotic surgical system to aid in avoiding contact with neural tissue while accessing the spine. Alternatively, systems, methods, and devices of the present invention can be used as a standalone pre-operative planning system. For example, an image analysis tool of the present invention, along with the systems and methods described herein, can be used as a pre-operative planning system in conjunction with pre-operative CT scanning. Whether used as a stand-alone or incorporated into an intra-operative environment, an image analysis tool of the present invention can rely on CT or CBCT images alone to identify and segment neurological tissue of a patient in a scanned surgical region, and does not require additional imaging, such as MRI or ultrasound, to be performed on the patient for the purposes of identifying and locating neural tissue in the surgical region.

An image analysis tool of the present invention can generate and output a 3D model of predicted neural tissue near the spine of a patient using a deep-learning based covariation model of neural and musculoskeletal anatomy. FIG. 1 shows an exemplary 3D model output 10 of the image analysis tool of the present invention. The 3D model 10 can be a visual representation of segmentation data calculated by the image analysis tool. As will be discussed in greater detail below, a data output of the image analysis tool can be converted into a surface model using a segmentation to surface model conversion algorithm such as marching cubes. It will be appreciated that any known method of converting segmentation data to a visual model can be used and is within the scope of the present invention.

The exemplary output 10 is a 3D model visualizing a spinal region of a patient which has been automatically segmented by an image analysis tool to identify neurological structures in the spinal region. The 3D model output 10 illustrated in FIG. 1 displays two adjacent vertebrae, 20 and 30, with a visualization of predicted neural tissue 40 of the spinal region. In one embodiment, an image analysis tool can identify and output within the 3D model 10 at least one confidence interval 50. A confidence interval can account for expected sources of error in the predicted location of nerves. Calculation error can result, for example, from natural patient variation or measurement error. The confidence interval of the image analysis tool can be an iso-surface that represents confidence intervals for a location of neurological tissue.

A brief overview of an image analysis tool of the present invention will now be provided, followed by a description of methods of using an image analysis tool of the present invention. Finally, the image analysis tool of the present invention itself will be discussed in detail.

An image analysis tool of the present invention can include a segmentation algorithm that can receive as an input unlabeled CT or CBCT scan data and can predictably locate and identify neurological structures in the scanned region. The segmentation algorithm can rely on a trained deep-learning covariation model between neural tissue and anatomical structures. The covariation model includes complete data, i.e. segmented bones, muscle, and neural anatomy, and can be used to predict missing data labels, i.e. neural anatomy from a CT or CBCT scan. The image analysis tool receives as an input an unlabeled patient CT or CBCT scan and uses the segmentation algorithm to locate and identify the neural tissue in the scanned region. The image analysis tool can generate and output a 3D model volume of the input scan region identifying the labeled neurological structures. Additionally, the image analysis tool can be configured to output labeled musculoskeletal structures present in the unlabeled CT or CBCT input scan.

A covariation model of the present invention is initially created during an offline training phase of an image analysis tool. The training phase, as will be discussed in detail below, uses input data of labeled MRI volumes to build an anatomical co-variation model. The training phase can also include additional training data generated from the MRI volumes to train the model. The co-variation model is then used to train the image analysis tool on a second set of input training data. The second set of input training data can be labeled CT or CBCT volumes, i.e. CT or CBCT volumes including segmented musculoskeletal structures. The image analysis tool can then use the co-variation model to output neurological structures corresponding to the labeled musculoskeletal anatomy. After the offline training phase, the image analysis tool can be deployed in various systems and methods of the present invention to identify neural tissue in a surgical region of a patient from unlabeled CT or CBCT scan volumes.

Figure 2:
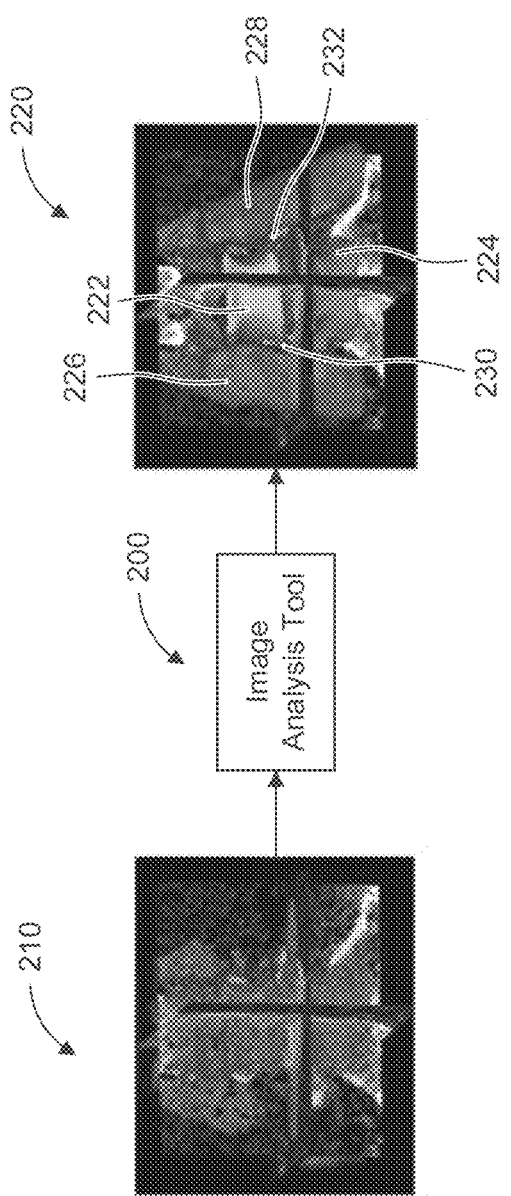
FIG. 2 illustrates an exemplary embodiment of a deployment scheme of a trained image analysis tool of the present invention.

Turning to the deployment, or use, phase of an image analysis tool of the present invention, FIG. 2 illustrates a deployment scheme of a trained image analysis tool 200. The image analysis tool 200 can receive as an input a patient scan 210. The input patient scan 210 can be a completely unlabeled or unsegmented image volume. The input patient scan can be a pre-operative patient scan or an intra-operative patient scan. In one embodiment, the image analysis tool 200 can receive gray level data of a CBCT volume, voxel data of a CT volume, or an equivalent unlabeled or unsegmented image data representing a scanned patient anatomy using any imaging technology known in the art. In the example shown in FIG. 2, the trained image analysis tool 200 receives a gray level data CBCT volume 210 of a patient spinal region.

The image analysis tool 200 can use a segmentation algorithm to automatically segment musculoskeletal tissue and neurological tissue of the received input data. For example, an output 220 of the image analysis tool 200 can show segmented musculoskeletal tissue, such as vertebral bodies, intervertebral discs, psoas muscles, and erector spinae muscles, and neurological tissue, such as nerves, spinal cord, and cauda equina. For example, the output 220 of FIG. 2 shows segmented musculoskeletal tissue, vertebrae 222 and 224 and psoas muscles 226 and 228, and neurological structures, exiting nerve roots 230 and 232. An image analysis tool of the present invention can display multiple regions of identified neurological structures based on a statistical analysis and a covariation model as well as patient phenotype information. Patient phenotype information can include, for example, patient gender, body-mass-index, foraminal space, etc.

As discussed above, the output 220 of an image analysis tool of the present invention can be a 3D surface model with at least one neurological structure identified and labeled. The 3D surface model can be realized using a segmentation to surface model conversion algorithm. An image analysis tool or a system incorporating an image analysis tool of the present invention can display the identified neurological structures and overlay the neurological structures on the input scan volume, i.e., an unlabeled CT or CBCT scan.

Figure 3:
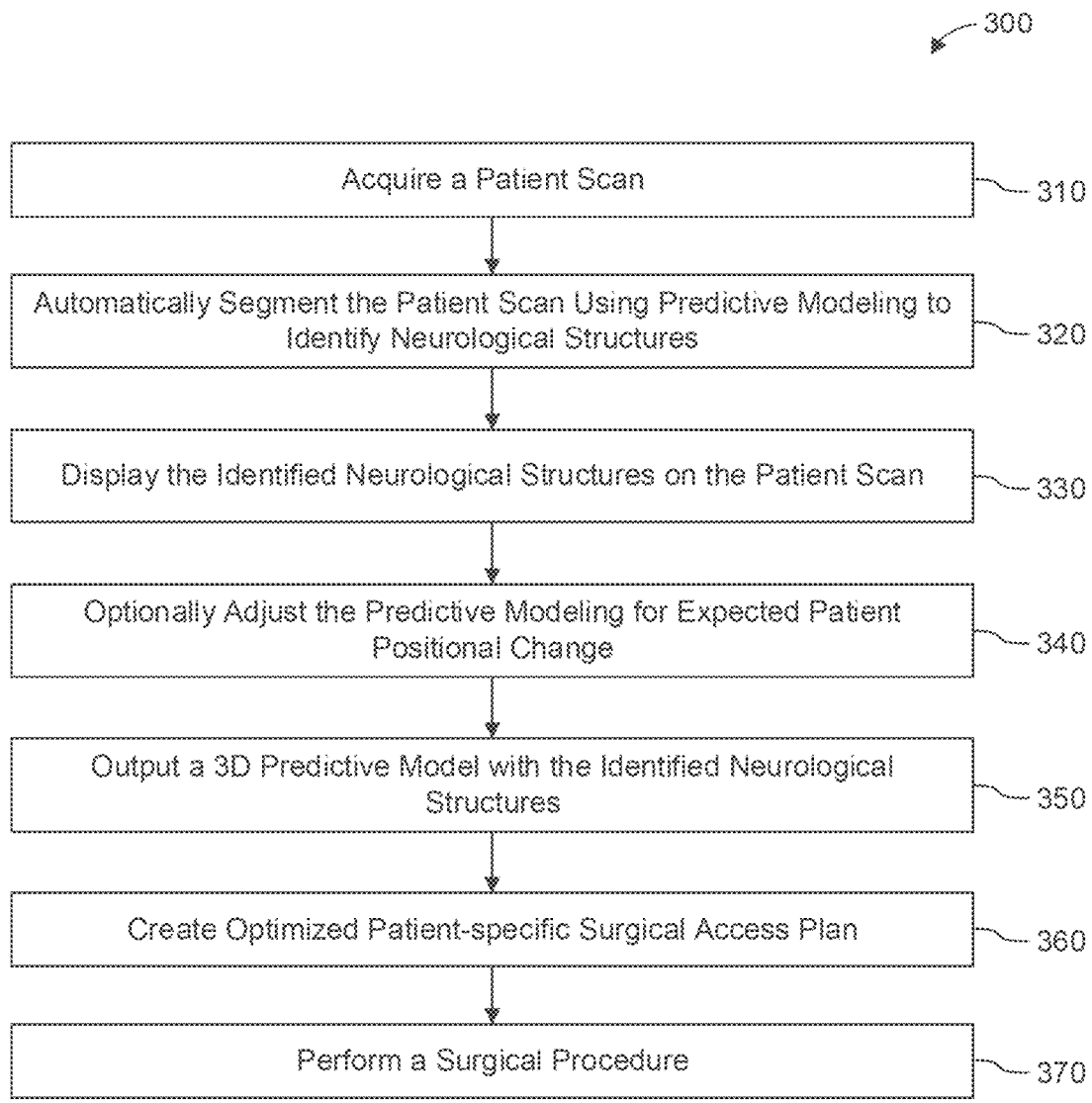
FIG. 3 is an exemplary method of creating a patient-specific surgical plan using an image analysis tool of the present invention.

FIG. 3 illustrates an exemplary method 300 of using an image analysis tool of the present invention to create a patient-specific surgical plan. The patient-specific surgical plan can be a plan optimized to reduce the risk of contacting neurological tissue. The patient-specific surgical plan created with a method 300 can be used as a stand-alone pre-operative planning tool or can be incorporated intra-operatively while performing a surgical procedure. In a first step 310, a CT or CBCT volume of a surgical region is acquired by the image analysis tool. As previously discussed, the CT or CBCT volume acquired by the image analysis tool can be unlabeled. Next, in step 320, the image analysis tool can automatically segment and identify neurological structures of the acquired patient scan input volume. Additionally, the image analysis tool can automatically segment and identify musculoskeletal structures of the input volume. The identified neurological structures can then be displayed and overlaid on the CT or CBCT input volume at step 330.

In one embodiment, an image analysis tool can account for expected movement of the neurological structures based on expected changes in patient position in step 340. For example, expected changes in patient position can be a change between a patient imaging position and a patient operation position. For example, if an input CT scan is taken in a supine position and an operation will be performed in a prone position, the system can account for this positional change and update a predicted location of neurological structures. The displayed neurological structures can be updated, adjusted, or initially reflect an expected change in patient position. Information regarding a change in patient position can be loaded into the system either before or after neurological structures are initially identified. Positional information can be input into the system using any known method of data entry, for example by selecting a patient position from a drop down list, by directly entering in patient position information in a data entry form, or by the image analysis tool system automatically retrieving positional information from information stored on a connected network, server, or other data location. Neurological tissue models can be output by the image analysis tool system at step 350 reflecting the predicted and visualized location of neurological tissue in a patient specific spinal surgical region. It will be appreciated that neurological tissue models can be output before, after, or both before and after an adjustment is made to the predictive location of the neurological tissue based on a change in patient position.

At a step 360, a patient-specific optimal surgical plan can be generated from the predictive modeling of neurological structures output by the image analysis tool. In one embodiment, the patient-specific optimal surgical plans can be plans for accessing a disc space or spine while avoiding contact with neurological tissue. In one embodiment, the image analysis tool can identify a recommended safe access zone. The safe access zone can be an area or areas with nerve existence probabilities of less than a predetermined threshold, thus representing a safe path for surgical instrumentation to pass during surgery. In one embodiment, the optimal surgical plans can be displayed superimposed with specific tools required for the procedure. For example, the optimal surgical plans can show an access portal, a pedicle screw, or any other instrumentation planned for use in a surgical procedure near predicted neural tissue.

A patient-specific optimal surgical plan generated in association with a predictive modeling by an image analysis tool of the present invention can then be used to perform a surgical procedure with a reduced risk of neurological complications, step 370. In one embodiment, the optimal surgical plan can be used as an input into a robotic surgical system to assist in planning a tool path to avoid damaging neural anatomy while accessing the spine, performing bone cutting, discectomies, and the like. Alternatively, or in addition to use with a robotic surgical system, the patient specific optimal surgical plan can be used intra-operatively in conjunction with neural monitoring probes or cameras to verify location of neurological structures. The generated patient specific optimal surgical plan can also be used as a standalone pre-operative planning system with CT imaging to prepare for a surgical procedure.

Figure 4:
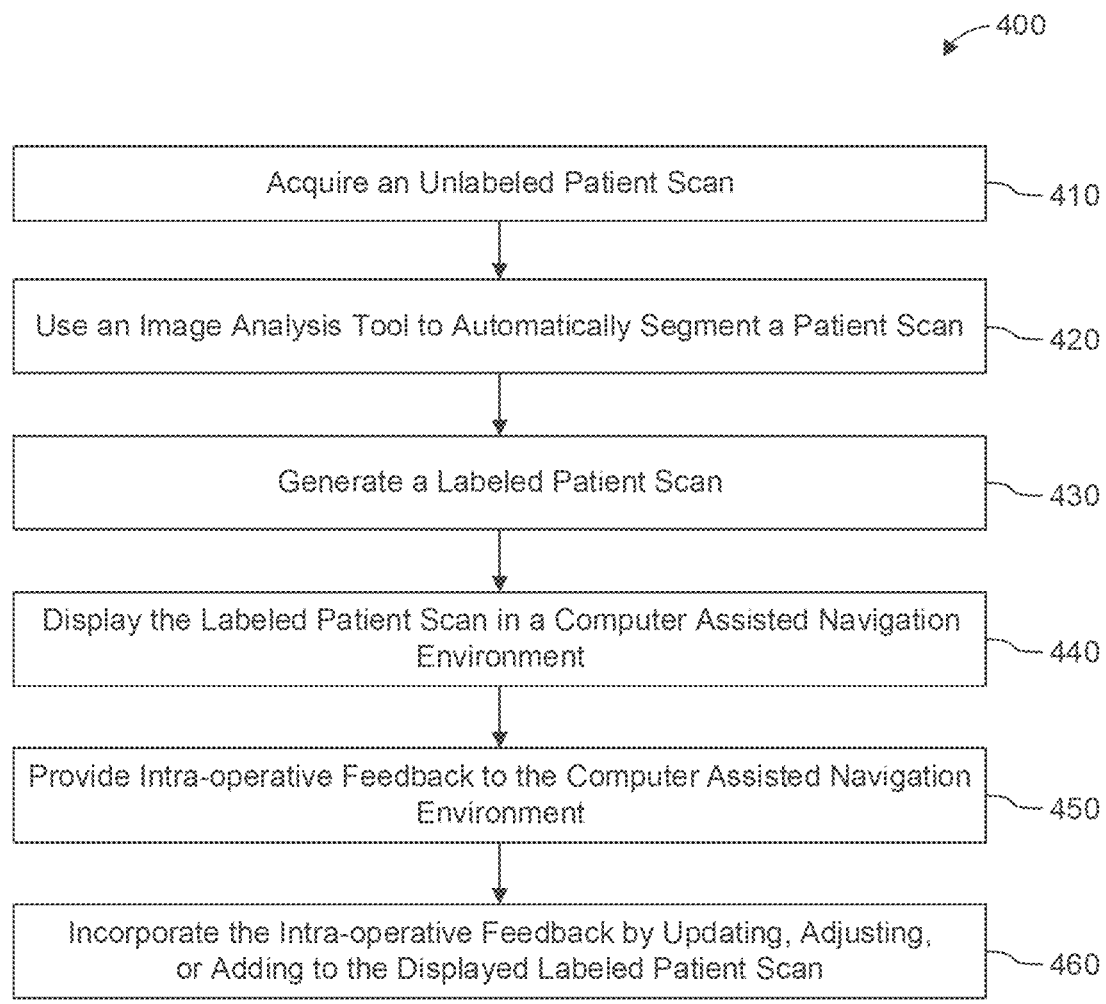
FIG. 4 is an exemplary method of intra-operative use of an image analysis tool of the present invention.

In another exemplary embodiment, an image analysis tool system of the present invention can be used intra-operatively as part of a computer assisted navigation environment. The computer assisted navigation environment can include additional technology for aiding in a surgical procedure, such as, for example, CBCT imaging technology, tool tracking, neural location probes, cameras, and the like. FIG. 4 represents an exemplary method 400 of an intra-operative use of the image analysis tool of the present invention, while FIGS. 5-10 illustrate steps of the exemplary intra-operative use of the image analysis tool of FIG. 4.

Figure 5:
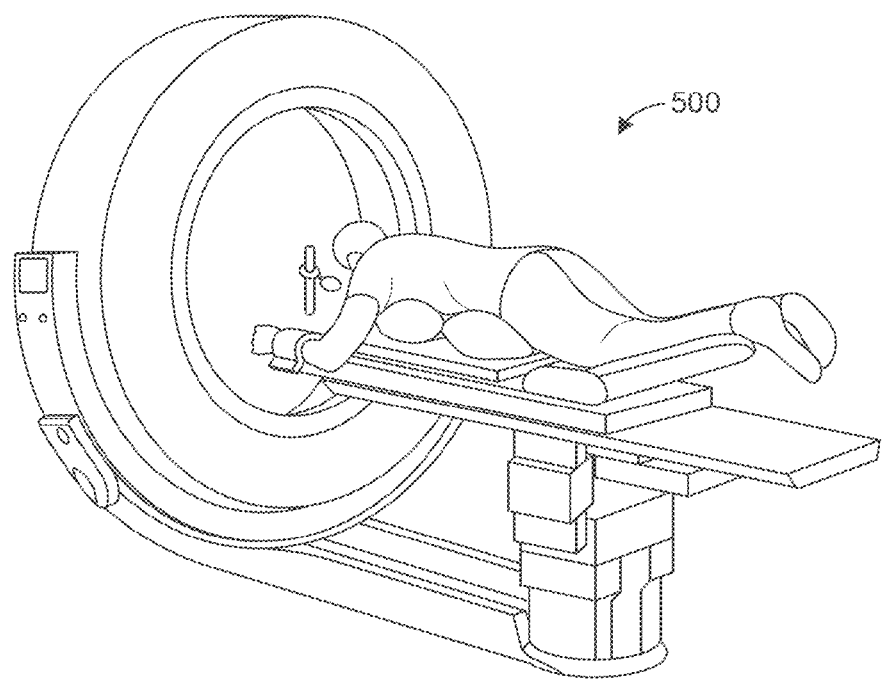
FIG. 5 is an exemplary illustration of a step of the method of FIG. 4.
Figure 6:
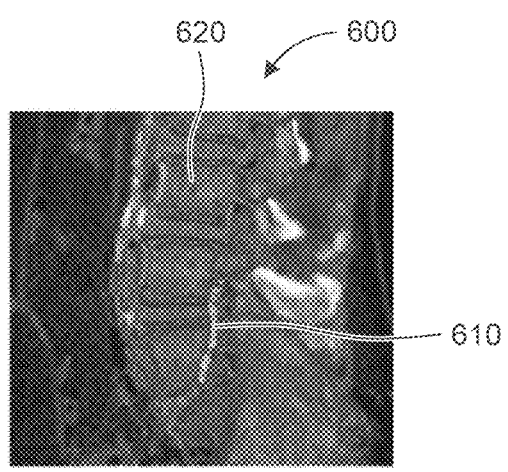
FIG. 6 is an exemplary illustration of a step of the method of FIG. 4.

In a first step, 410, an image analysis tool can acquire an unlabeled patient scan volume as an input. In one embodiment, the patient scan can be an intra-operative CT or CBCT scan of a patient's spine. Alternatively or additionally, the patient scan can be a pre-operative scan of a patient's spine. The patient scan can be taken with the patient in a supine, prone, or semi-prone position depending on the specifics of a surgical procedure and a surgical approach. FIG. 5 illustrates an intra-operative CBCT scan of a patient 500 in a prone position. After the unlabeled patient scan volume is acquired by the image analysis tool, the image analysis tool can automatically segment the scan volume to identify and label neurological tissue in the unlabeled input scan, step 420. The image analysis tool can also segment musculoskeletal tissue in the unlabeled input scan. For example, the image analysis tool can automatically segment and label neural tissue, vertebral bodies, and other musculoskeletal tissue, such as the erector spinae muscles and psoas muscles, in the input image volume. FIG. 6 shows an exemplary patient scan that has been automatically labeled by the image analysis tool. As will be described in detail below, the image analysis tool can identify and label neurological and musculoskeletal tissue on an unsegmented image volume using a deep learning based anatomical co-variation model. FIG. 6 shows a slice of a 3D volume output by the image analysis tool of the present invention. In particular, a neurological structure 610, i.e., an exiting nerve root 610, can be identified and overlaid on the now automatically segmented input scan volume 600. The image analysis tool can also identify and model musculoskeletal tissue 620. In one embodiment, a segmented output such as slice 600 can be displayed on a screen or display of a computer assisted navigation environment.

Next, an optimized patient-specific surgical plan can be created in step 430 from the segmented image analysis tool output. The optimized patient-specific plan can take into account patient anatomy as well as surgical goals and surgical constraints. For example, for a lateral trans-psoas surgical procedure, an optimized trajectory can be planned that maximizes access to a disc space and relevant boney structures while minimizing contact with surrounding nerve roots and nerve tracks embedded in the psoas muscle particular to a particular patient. Neurological structures corresponding to a scanned surgical region can be identified by the image analysis tool and accounted for in creating the optimized surgical plan. It will be appreciated that steps 410-430 can be performed pre-operatively, intra-operatively, or a combination of pre- and intra-operatively.

Figure 7:
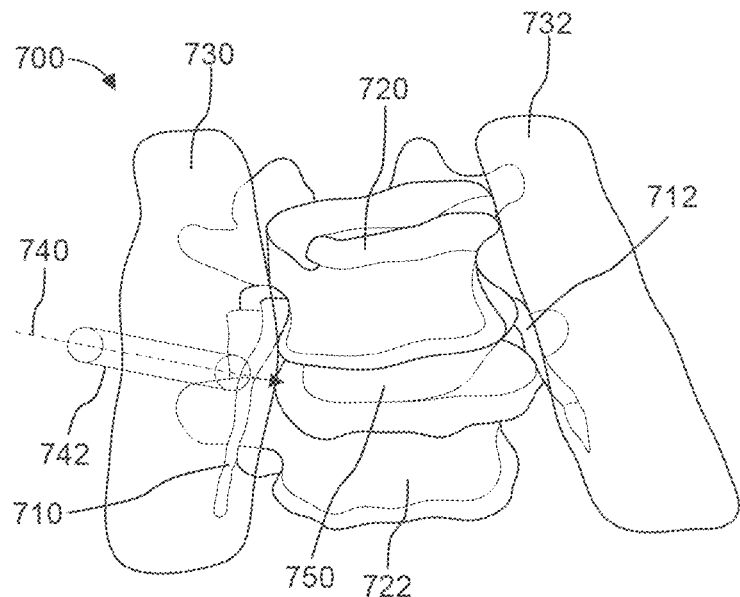
FIG. 7 is an exemplary illustration of a step of the method of FIG. 4.

FIG. 7 shows an exemplary patient-specific optimized surgical plan. In particular, FIG. 7 shows an optimized table trajectory for accessing a vertebral body space of a particular patient. The 3D model 700 is an output of an image analysis tool system and can display the automated segmentations generated by the image analysis tool. For example, the 3D model 700 can include a first nerve bundle or nerve branch 710 and a second nerve bundle or nerve branch 712 exiting a spinal region of the patient. In particular, the nerve branches 710, 712 can be seen exiting a region near two adjacent vertebrae, 720 and 722. Muscle tissue in the spinal region, such as psoas muscles 730 and 732, can also be segmented and labeled by the image analysis tool. The system and labeled 3D volume can then be used to plan an optimal trajectory 740 for a particular surgical procedure. The optimal trajectory 740 can represent an optimal path for a surgical instrument to access a surgical region. In the exemplary embodiment shown in FIG. 7, the optimal trajectory 740 shows an access path to an intervertebral space 750 to avoid neurological structure 710. A safe access zone 742 can also be generated by the image analysis tool system. A safe access zone can represent an area where the existence of neural tissue is below a predetermined threshold. In other words, an identified safe access zone can represent a predicted area where surgical instrumentation can safely pass with a reduced risk of contacting a neurological structure.

Figure 8:
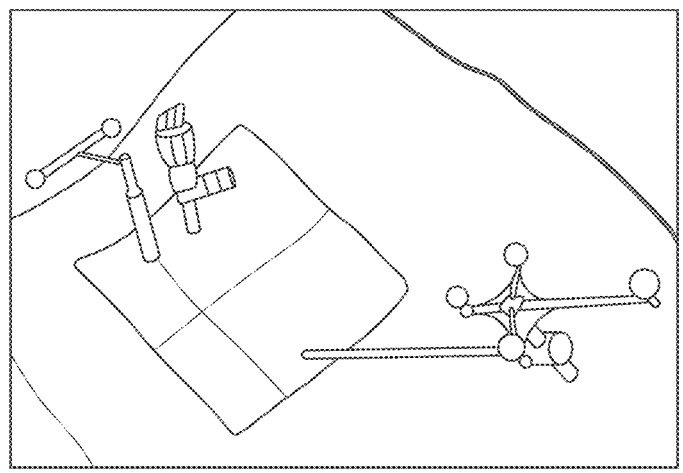
FIG. 8 is an exemplary illustration of a step of the method of FIG. 4.

In a step 440, a patient-specific surgical plan can be shown as part of a computer assisted navigation environment display. An image analysis tool of the present invention can be in communication with a surgical navigation environment. Alternatively the image analysis tool can be initially programmed into or created with the surgical navigation device. The surgical navigation environment can include both patient and instrument arrays for tracking tools, such as Jamshidi-type needles, with respect to the intra-operative CBCT image volume. The surgical navigation environment can display real-time feedback of positioning of both the patient and tools used in a surgical procedure. The patient and instrument array feedback can be displayed overlaid or integrated with a CBCT image volume output and/or an optimized surgical plan. FIG. 8 shows an example of a surgical procedure being performed on the patient 100, where a plurality of surgical instruments are used to access the patient's spine using a minimally invasive technique. Note that the plurality of instruments can be tracked by, e.g., a surgical navigation system, to enable registration to, and execution based on, the 3D model for the procedure shown in FIG. 7.

In step 450, intra-operative feedback can be provided to the computer assisted navigation environment while a surgical procedure is being performed. For example, a surgical instrument can be navigated into an intervertebral disc space following an optimized patient-specific surgical access plan. In on embodiment, the surgical instrument can include a tool tracking array or a sensor to transmit location information back to the computer assisted navigation environment. By way of further non-limiting example, a surgical instrument can provide feedback, such as visual feedback, ultrasonic feedback, etc., to the computer assisted navigation environment on a location of neurological structures, surgical instrumentation, additional patient anatomy, and the like.

In one embodiment, an ultrasound based nerve localization probe can provide intra-operative feedback regarding positioning of at least one neurological structure in a surgical region. A displayed patient scan volume can be updated or adjusted based on the intra-operative feedback. In other embodiments, other nerve localization instruments can be utilized in place of an ultrasound probe, including, for example, mechanomyography (MMG), electromyography (EMG), and other known instruments for detecting the presence of nerve tissue.

In a step 460, the intra-operative feedback can be communicated to a user. For example, a displayed patient scan labeling neurological structures can be updated, revised, or adjusted to reflect the intra-operative feedback. In this way, an embodiment the present invention configured for intra-operative use with a computer assisted navigation environment can provide visual feedback regarding at least one of a location of neurological tissues in a surgical region, a deviation of a surgical instrument from a pre-planned path, a relative location of a surgical instrument to a neurological structure, etc. In one embodiment, the computer assisted navigation environment in conjunction with the image analysis tool of the present invention can continuously refine and update a nerve map based on information obtained from auxiliary surgical instrumentation. By way of non-limiting example, the auxiliary surgical instrumentation can include auxiliary nerve localization systems, such as triggered MMG, optical, or ultrasound based hand held nerve localization systems. The nerve map can also be updated if CT or CBCT scans are updated based on patient movement.

Figure 9:
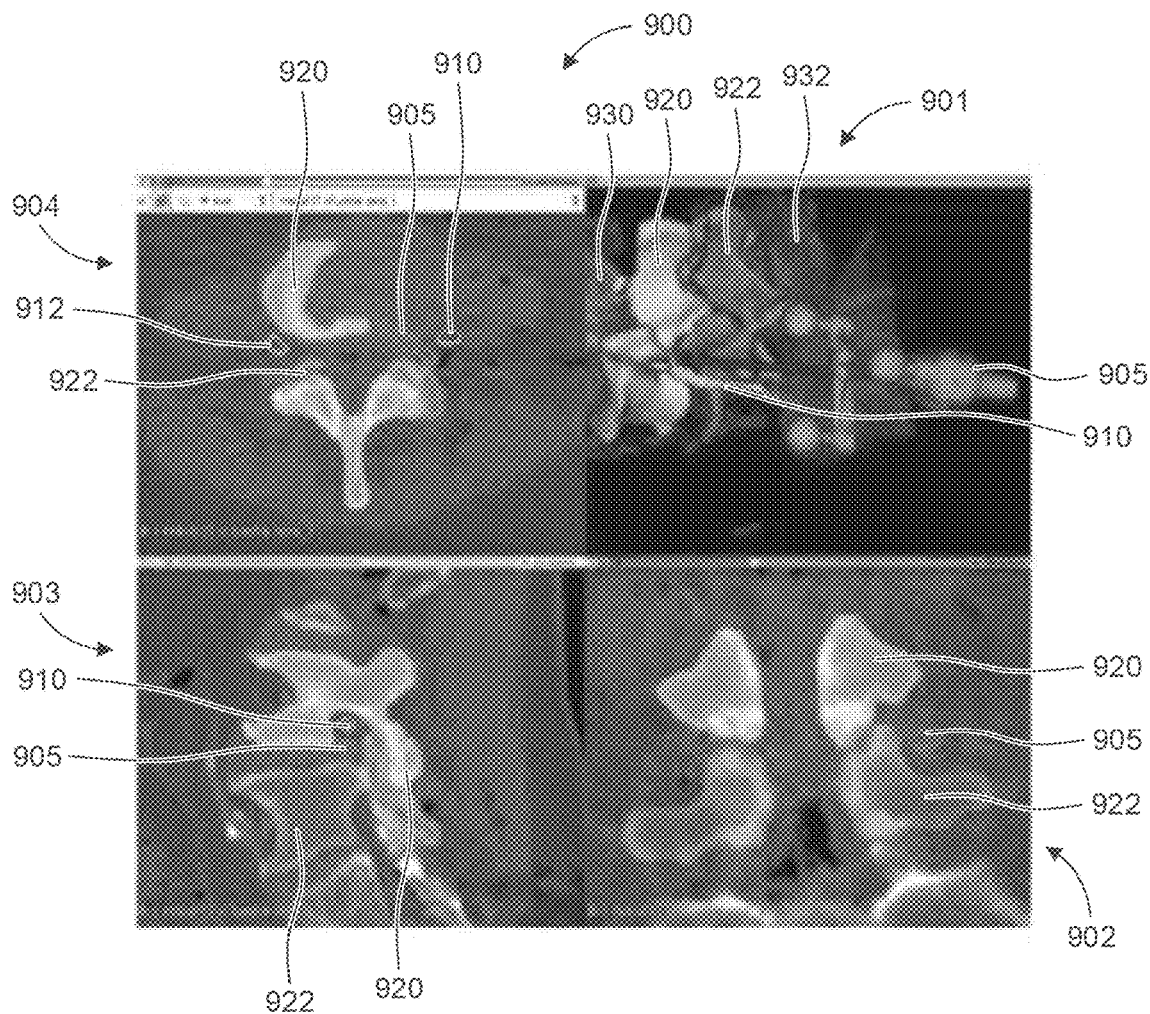
FIG. 9 is an exemplary illustration of a step of the method of FIG. 4.
Figure 10:
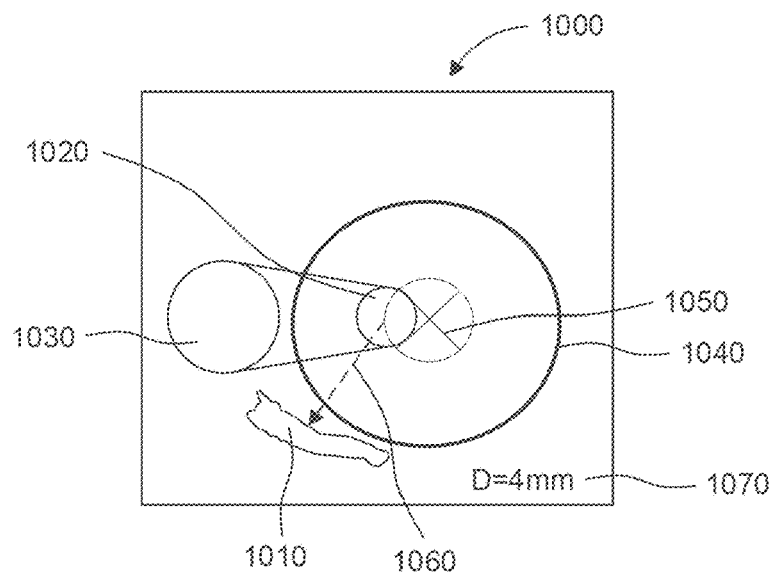
FIG. 10 is an exemplary illustration of a step of the method of FIG. 4.

As can be seen in FIGS. 9 and 10, a computer assisted navigation environment can provide real-time or near real-time visual feedback regarding the surgical procedure. For example, feedback can be displayed on the surgical navigation environment reflecting distance of an instrument to the nearest neurological structure or deviation from a planned optimal trajectory or an optimal instrument path. FIGS. 9 and 10 show two exemplary displays of a surgical navigation environment incorporating real-time surgical feedback with outputs generated by the image analysis tool of the present invention. In FIG. 9, an exemplary surgical navigation environment display 900 is shown comprising four different views showing a probe 905 relative to anatomical structures of the patient. By way of non-limiting example, the surgical navigation environment can display a 3D model of the patient anatomy and surgical instrumentation, such as display 901, along with several 2D views of the patient anatomy and surgical instrumentation from different orientations, for example views 902-904. In particular, the probe 905 can be seen in the generated views relative to the automatically labeled portions of the image analysis tool output volume, i.e. labeled bone volumes 920 and 922, labeled muscle volumes 930 and 932, and labeled neurological tissue 910 and 912. As a probe 905 is manipulated within the imaged surgical region, the motion and an accompanying change in position can be reflected on the display of a computer assisted navigation environment.

FIG. 10 shows another exemplary display of a surgical navigation environment system including an image analysis tool of the present invention. For example, a surgical navigation environment can generate and display a surgical instrument's motion within a surgical region relative to an optimized trajectory and/or identified neurological structures. For example, a display 1000 can provide real-time feedback regarding a location of a probe 1020 to a neurological tissue 1010. The display 1000 can show a top view or a bird's eye view of a surgical region looking down on an optimal trajectory path 1050. The displayed optimal trajectory path 1050 can be generated from the image analysis tool system as described above. In one embodiment, the display 1000 can also show a safe access zone 1040 around the optimal trajectory 1050. A trajectory 1030 of the probe 1020 can also be displayed. In one embodiment, the surgical navigation environment can use the predictive modeling of the image analysis tool and real-time feedback provided by a tool tracking array or a sensor to calculate a shortest distance from the probe 1020 to a closest neurological structure, in this case neurological tissue 1010. An on-screen visualization can indicate the shortest distance between the probe and the closest neurological tissue. In the exemplary embodiment of FIG. 10, this distance can be represented by an arrow 1060 and an indication of distance 1070, for example 4 mm.

Figure 11:
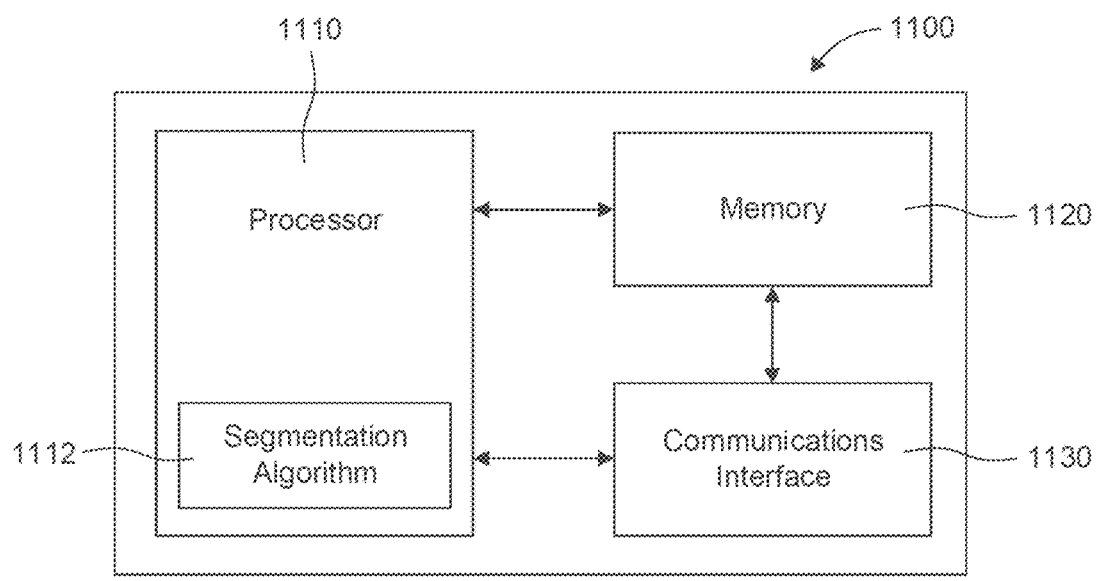
FIG. 11 is an exemplary schematic illustration of an image analysis tool of the present invention.

The image analysis tool will now be discussed. Turning now to the construction and training of an image analysis tool of the present invention, FIG. 11 shows a schematic representation of an exemplary image analysis. The image analysis tool can include one or more components for receiving, processing, communicating and/or storing image data and information relating to a surgical procedure, a patient, and the like. As schematically illustrated in FIG. 11, an exemplary image analysis tool 1100 can include a processor 1110, a memory 1120, and a communication interface 1130—all of which can be in communication with each other. Further, although each of these components are referred to in the singular, it will be appreciated by a person skilled in the art that the various functions described as being carried out by one of these components can actually be carried out by multiple of those components, e.g., the functions described as being carried out by the processor 1110 can be carried out by multiple processors.

The processor 1110 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor 1110 can be configured to generate information identifying, locating, modeling and/or visualizing anatomical structures, for example neurological structures, in an imaged region of a patient anatomy and/or perform various calculations based on information received from an external device via the communications interface 1130, information directly input into the communications interface 1130 by a user, and/or information stored in the memory 1120. By way of non-limiting example, the processor can be configured to identify and locate neural tissue in an unlabeled image volume, generate a 3D volume of a surgical region identifying neurological anatomy, build a deep-learning anatomical covariation model, etc.

The processor 1110 can be coupled to the memory 1120, which can include a random access memory (RAM), a read-only memory (ROM), a flash memory, a non-transitory computer readable storage medium, and so forth. The memory 1120 can store instructions for execution by the processor 1110 to implement the systems disclosed herein or to execute the methods disclosed herein. Additionally or alternatively, the memory 1120 can store information generated or calculated by the processor 1110 and/or received from an external device or directly input through the communication interface 1130.

The communication interface 1130 can be configured to receive and transmit information from or to any of the processor 1110, the memory 1120, a direct input module 1140, and one or more external devices 1150, e.g., a sensor, a surgical instrument, an imaging device, a computer assisted navigation environment system, a robotic surgical system, a computer or processing device, etc. The communication interface 1130 can be wireless (e.g., near-field communication (NFC), Wi-Fi, Bluetooth, Bluetooth LE, and the like) or wired (e.g., USB or Ethernet). In one embodiment the communication interface 1130 can be configured to meet the Digital Imaging and Communications in Medicine (DICOM) standard to receive, communicate, and manage medical imaging information and related data. In another exemplary embodiment, the communication interface 1130 can be in communication with a sensor, a surgical instrument, an imaging technology, or the like, to receive intraoperative feedback. By way of non-limiting example, the communication interface 1130 can receive real-time intraoperative positional data from an external device regarding positional information of at least one of a surgical instrument, neural tissue, patient positioning and the like.

As discussed above, an image analysis tool of the present invention can be used to locate and identify neural tissues in a scanned image volume of a patient to aid in the navigation of surgical instruments and reduce the chance of neurological injury during spinal surgery. The image analysis tool can be configured as a machine learning tool, relying on at least one deep-learning based model that can be trained in order to predictively locate and visualize anatomical structures. A processor 1110 can contain a segmentation algorithm 1112. The segmentation algorithm 1112 can be configured to receive an unlabeled patient scan volume that does not show neurological anatomy and, based on a trained anatomical co-variation model, can automatically segment and identify neurological structures present in the scanned volume. The segmentation algorithm can further be configured to identify unlabeled structures that are shown in the imaging volume, such as musculoskeletal structures. In one embodiment, the segmentation algorithm 1112 can be a deep neural network with multiple layers between an input and an output layer. The segmentation algorithm can be trained to decompose images of training data, identify trends that exist across all sample images, and classify new images without human input by relying on the learned training data.

The segmentation algorithm 1112 can be based on anatomical co-variation associations between neural tissues, typically not visible in a CT or CBCT image, and musculoskeletal structures that are visible in a CT or CBCT image. In an application focusing on a spinal region, for example, visible musculoskeletal structures in a spinal CT or CBCT image can include vertebral bodies, osteophytes, psoas muscles, erector spinae muscles, etc. MRI image volumes, on the other hand, show both musculoskeletal structures and neurological structures. As such, MRI image volumes can aid in illustrating the concept of anatomical co-variation between neurological structures and musculoskeletal structures in a spinal region. Furthermore, MRI image volumes can be used as a training data set to train a co-variation model of the segmentation algorithm 112.

Figure 12:
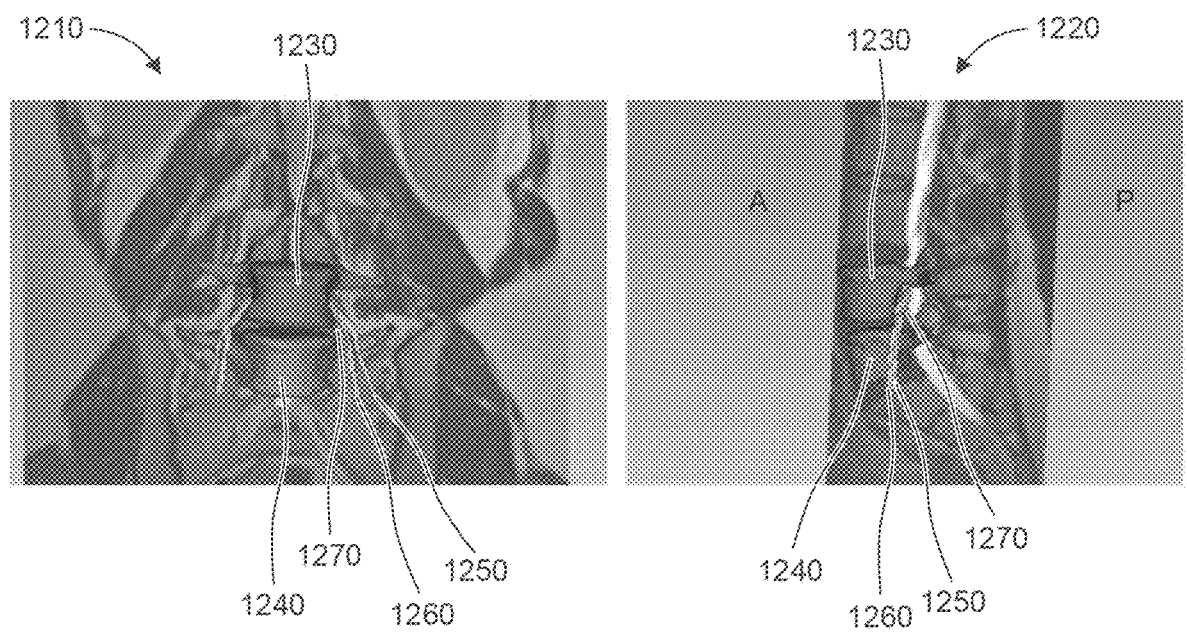
FIG. 12 illustrates fused MRI samples of a spinal anatomy.

FIG. 12 shows a visualization of inter-subject variation of neural anatomy in a lumbar spine region from three registered, or fused, patient MRI samples. The datasets were registered by applying an iterative closest point affine transform to the L4 and L5 vertebral bodies to correct for size, pose, and anisotropic shape differences between the three patients. The resulting transforms were then applied to nerves exiting an intervertebral space. The resulting fused MRI image volume is shown in FIG. 12 in a coronal plane view 1210 and a sagittal plane view 1220. Both musculoskeletal structures and neurological structures are shown segmented in the fused MRI image volume, since MRI images successfully capture both types of anatomical structures. For example, the fused MRI volume of FIG. 12 has been annotated to show first and second vertebral bodies 1230 and 1240. Three bundles of exiting nerve roots—1250, 1260, and 1270—can be seen in the MRI image volumes 1210 and 1220 exiting from the first vertebral body 1230. Each exiting nerve root bundle represents the anatomy of one patient in the fused MRI volume.

As can be seen in FIG. 12, after accounting for anatomical and positional variation in the L4 and L5 vertebral bodies, there is greater variation in the path of exiting nerves in the coronal plane than in the sagittal plane. This increased variation in the coronal plane can be due to inter-subject variation in the anatomy of the psoas muscles through which the exiting nerves travel. Thus, by modeling the co-variation among anatomical structures, i.e., muscles, bones, and neurological tissue, using complete data sets of patient anatomy, a deep-learning neural network can learn anatomical associations and predict a version of a missing component of a patient anatomy. Any spinal segment or patient anatomy can be analyzed in this manner to train an image analysis tool of the present invention. The systems and methods disclosed herein are not limited to analysis of an L4 and L5 spinal region. Furthermore, the system and methods disclosed herein are not limited to identifying neurological structures.

Figure 13:
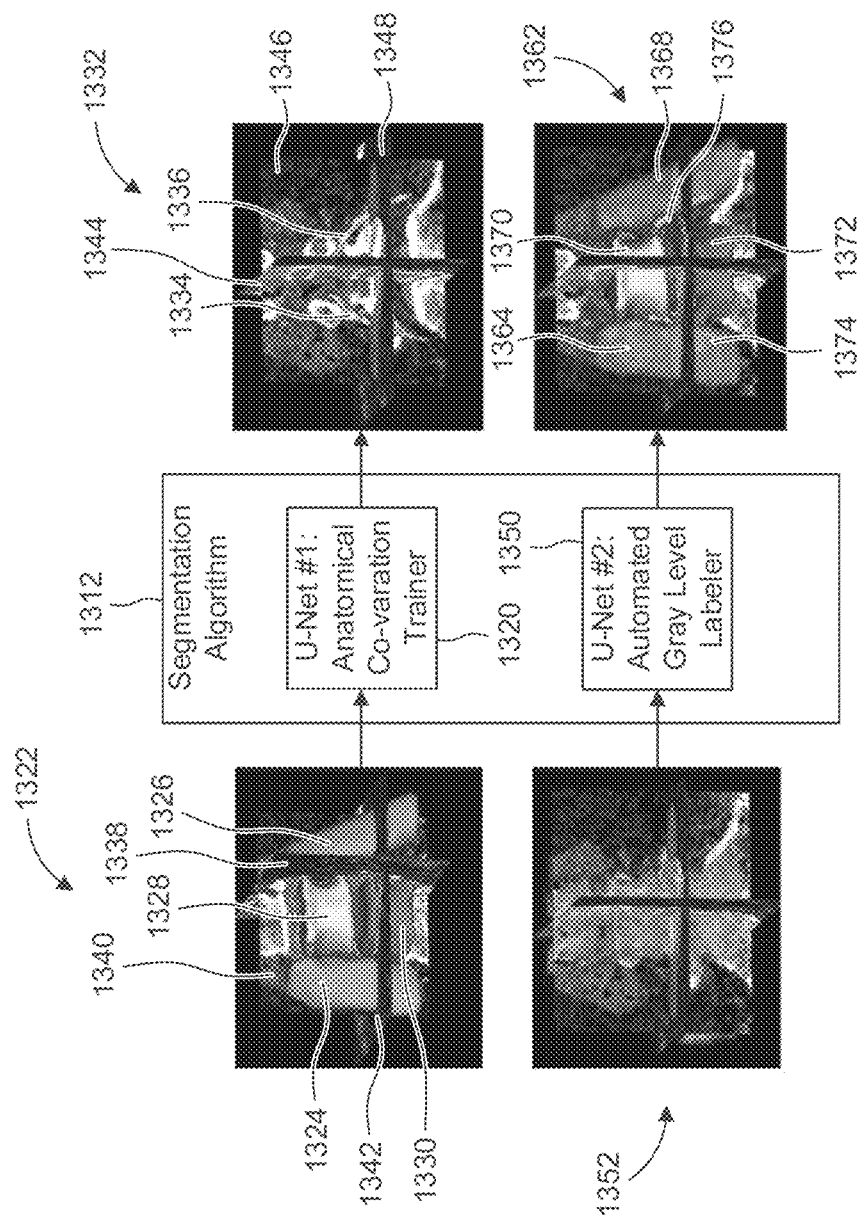
FIG. 13 is a schematic illustration of a segmentation algorithm of the present invention.

FIG. 13 shows a visual representation of an exemplary embodiment of a segmentation algorithm 1312 of an image analysis tool of the present invention. The segmentation algorithm 1312 can include a first U-Net 1320 and a second U-Net 1350. Together the first and second U-Net 1320, 1350 can enable the image analysis tool to predictively locate, identify, and visualize neurological structures from an unlabeled CT or CBCT image volume. The first U-Net 1320 can be configured as an anatomical co-variation model trainer. As will be described below, the first U-Net 1320 can be trained to receive a segmented CT or CBCT image volume as an input 1322. The input 1322 can be labeled to show musculoskeletal anatomy of a spinal region. For example, the input 1322 can include labeled muscle tissue, such as psoas muscles 1324 and 1326, and bone tissue, such as first and second vertebral bodies, 1328 and 1330. The first U-Net 1320 can then generate an output 1332 identifying at least one neurological structure that is not visible or captured in the input volume 1322 but associated with the imaged anatomy. For example, as shown in FIG. 13, the output 1332 of the first U-Net 1320 can label a first nerve bundle or branch 1334 and a second nerve bundle or branch 1336 in the imaged region of input 1322. Both input and outputs, 1322 and 1332, can include positional references to communicate information to a user. For example, input 1322 can display a sagittal reference plane 1338, a coronal reference plane 1340, and an axial reference plane 1342. Similarly, a sagittal 1344, coronal 1346, and an axial 1348 reference plane can be displayed on the output image volume 1332.

Figure 14:
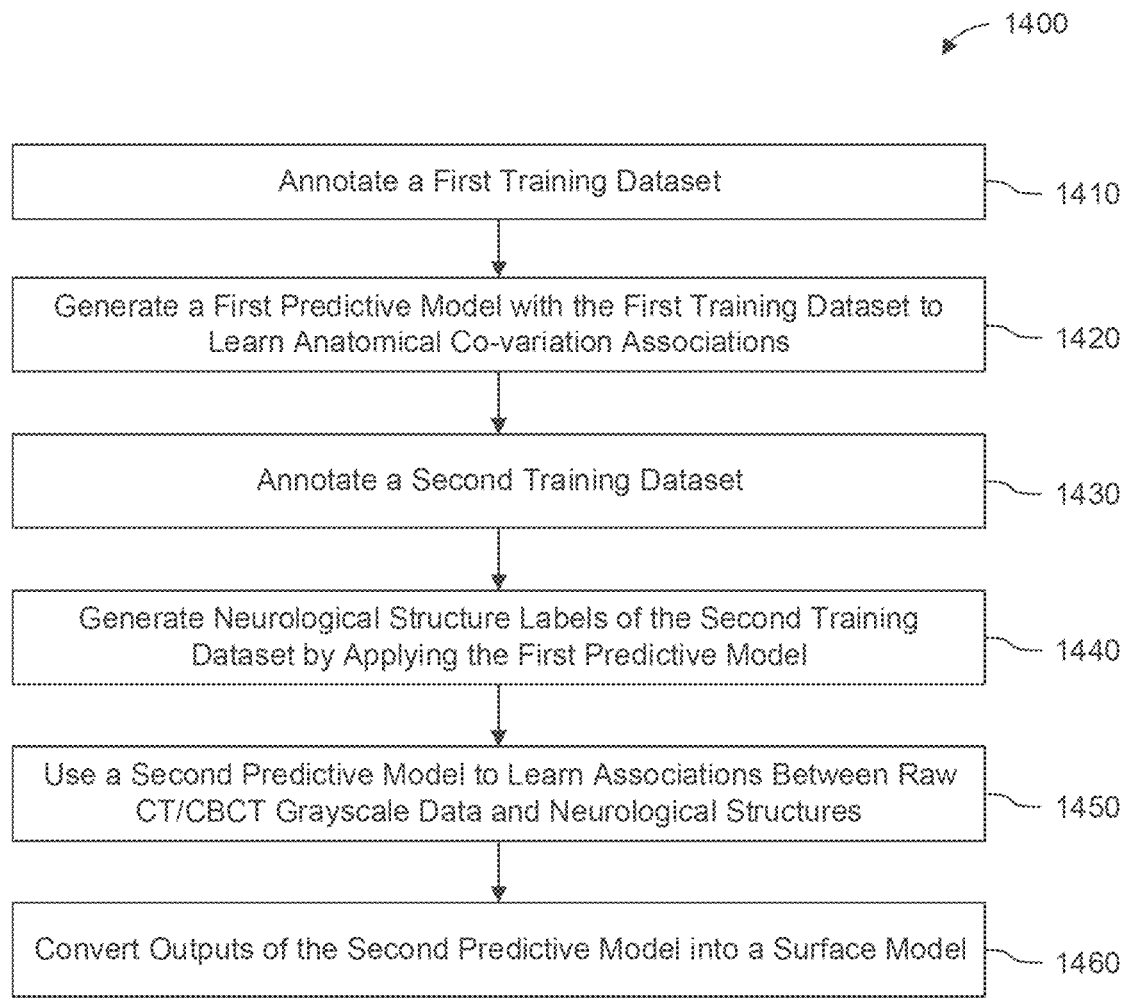
FIG. 14 is an exemplary method of training and deploying a segmentation algorithm of the present invention.

Training a first U-Net of the present invention will now be described with reference to FIG. 14. A method 1400 of FIG. 14 represents both a training phase and deployment phase of a segmentation algorithm of the present invention. Steps 1410-1440 can represent a training of a first U-net configured to be a co-variation model trainer. Steps 1460-1470 can represent a deployment of the segmentation algorithm, i.e., using a second U-net or predictive model to classify unlabeled image volumes. Training the first U-Net can include inputting a training database of segmented high quality MRI volumes from a representative patient population to teach the first U-Net associations between the segmented MRI volume components. In particular, the U-Net can learn associations between various segmented musculoskeletal structures and neurological structures of the MRI image volume. Training the first U-Net can also include inputting additional training data that has been generated from the high quality MRI volumes.

In a first step, 1410, a first dataset of MRI training volumes can be annotated or segmented to identify both neurological and musculoskeletal structures in each volume. In one embodiment, each type of structure can be further subdivided into subclasses. For example, musculoskeletal tissue of an MRI volume can further be identified as vertebral body, intervertebral disc, psoas muscle, spinae erector muscle, etc. Similarly, neurological tissue of an MRI volume can be broken into subclasses such as exiting nerve roots, nerve branches, spinal cord, cauda equine, lumbar plexus, etc. Preferably, a doctor, surgeon, nurse, healthcare professional, researcher, or other person(s) can manually annotate the input training volumes of the present invention. The first dataset can include at least one high quality MRI volume. In one embodiment the first dataset can be made up of a plurality of MRI volumes imaging a spinal region. Three-dimensional label maps can be produced for each tissue type, musculoskeletal and neurological, for each volume.

Figure 15:
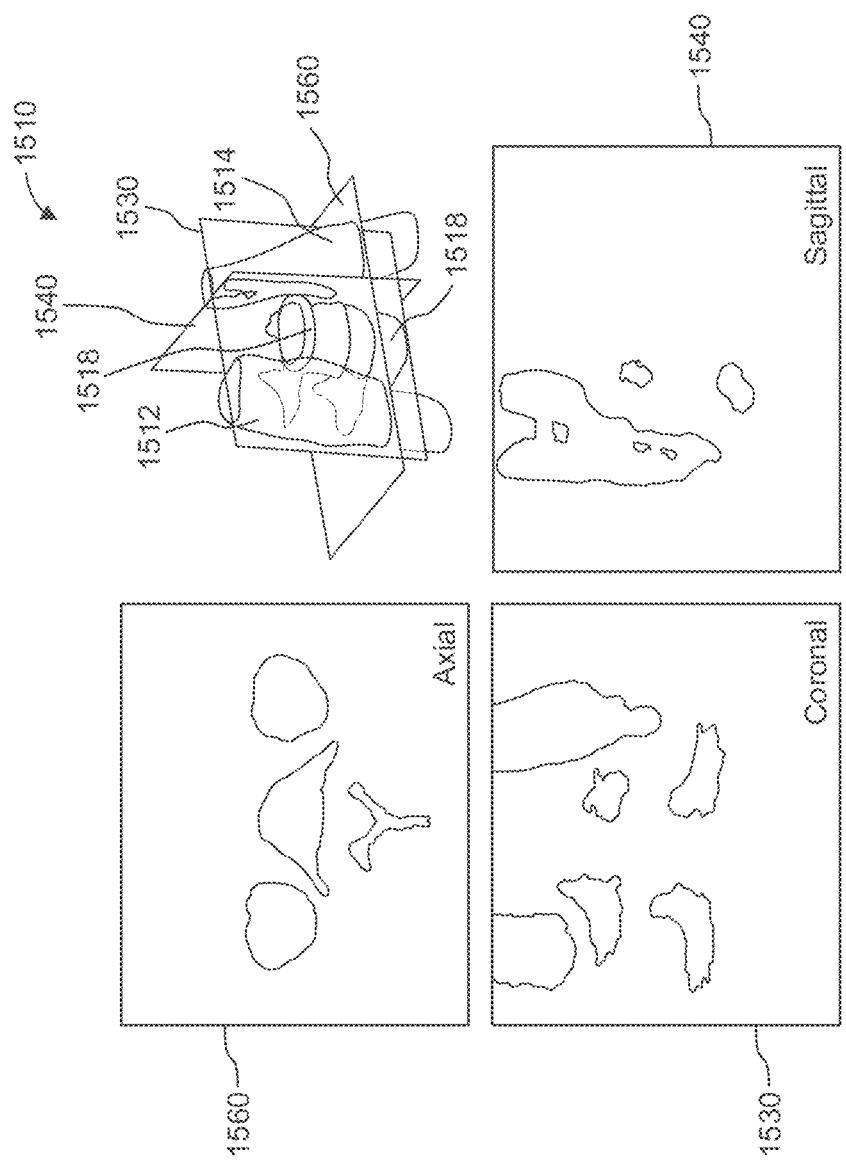
FIG. 15 shows an exemplary image volume input to a segmentation algorithm of the present invention.
Figure 16:
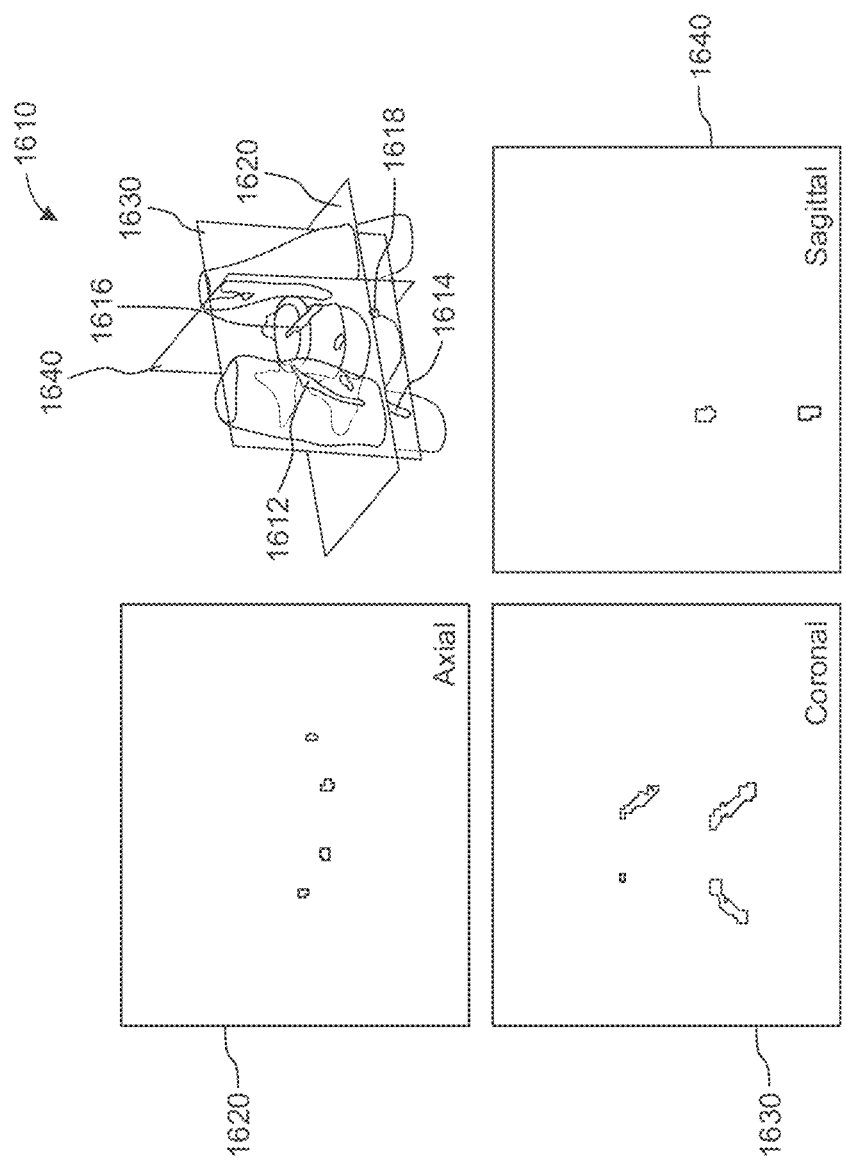
FIG. 16 shows another exemplary image volume input to a segmentation algorithm of the present invention.

Examples of annotated MRI volumes input as a training volume to train a first U-Net of the present invention can be seen in FIGS. 15 and 16. FIG. 15 illustrates an exemplary 3D annotated musculoskeletal map of an input training MRI volume. A three-dimensional annotated MRI volume 1510 shows a spinal region with a fully segmented musculoskeletal structure including psoas muscles 1512, 1514 and first and second vertebral bodies 1516, 1518. The annotated musculoskeletal structures can also be seen in two-dimensional slices of the MRI volume 1520. For example, a slice 1520 taken along an axial plane shows the psoas muscles 1512 and 1514 and the second vertebral body 1518. The annotated musculoskeletal structures of the MRI volume 1510 can also be seen in a slice 1530 taken along a coronal plane, a slice 1540 taken along a sagittal plane, and a slice 1560 taken along an axial plane. Each slice can show a view of the segmented musculoskeletal anatomy of MRI volume 1510.

Similarly, FIG. 16 illustrates an exemplary three-dimensional annotated neurological map of the same MRI volume of FIG. 15. In this exemplary embodiment, four neurological structures—1612, 1614, 1616, and 1618—have been identified and segmented in the MRI volume 1610. Two dimensional slices can be taken along different orientations of the MRI volume 1610. For example, a slice 1620 can be taken along an axial plane; a slice 1630 can be taken along a coronal plane; and a slice 1640 can be taken along a sagittal plane, to show different views of the segmented neurological structures identified in the MRI volume 1610.

A first training dataset can also include additional training sample data that is created by augmenting MRI volume data used as inputs in the first training dataset. For example, physics-based biomedical deformation transformations can be applied to the MRI volume data that represent different conditions such as, for example, a variation in patient position and variations in curvature and/or alignment of the spine, etc., to generate additional training data. The additional training datasets can then be annotated as described above with respect to the MRI volumes and used to train a first U-Net.

Turning back to FIG. 14, a first neural network, i.e. the first U-Net, can be trained with the annotated first training dataset to learn patterns of anatomical co-variation between musculoskeletal structures and neurological structures of an imaged region, i.e. a spinal region, in a step 1420. The learned patterns of anatomical covariation can create a deep-learning anatomical co-variation model. The deep-learning anatomical co-variation model can be a predictive model generated using a deep-learning neural network based on U-Net architecture. The basic structure of a U-Net architecture is known in the art. An image analysis tool of the present invention leverages the concept of a U-Net in an inventive manner to develop a tool which can use multiple U-Nets working together, such that an image analysis tool of the present invention is capable of receiving an unsegmented image volume, such as a CT or CBCT scan and outputting an image volume of the same region with labeled neurological structures not shown in the input image volume but corresponding to the image volume area.

In step 1420, the first neural network is trained on patterns between musculoskeletal structure and corresponding neurological structure of the spinal region by receiving the annotated first training dataset consisting of the labeled MRI volumes and/or any additionally created data samples, as described above. As annotated image volumes are input into the first U-Net, the U-Net can correlate labeled musculoskeletal pixels of an MRI image volume to corresponding labeled neurological structures of the same MRI image volume. In this way, the first neural network can create and update an anatomical co-variation model to learn new patterns and variations as the first neural network receives additional annotated data. It will be appreciated by one having ordinary skill in the art that the process of annotating a training dataset and training the first neural network can be an ongoing process. For example, additional MRI volumes can be annotated and input into the first neural network after an initial training of the first neural network.

A second training set of data is prepared in step 1430. The second training set can include CT or CBCT image volumes. As is known in the art, CT or CBCT image volumes are capable of showing musculoskeletal structures but they cannot image neurological structures in patient anatomy. The image volumes of the second training set can include the same segmented musculoskeletal tissue as the MRI image volumes of the first training dataset. In other words, the image volumes of the second dataset can correspond to the same imaged region of a patient anatomy as that of the first dataset. The image volumes of the second training set can be annotated to identify or segment the musculoskeletal structures present in the imaged volume.

In step 1440, the first neural network can use the anatomical co-variation model as a predictive model to classify unlabeled pixels and to generate neurological structure labels of neurological structures corresponding to the labeled musculoskeletal structures of the second training dataset. The CT or CBCT image volumes with labeled musculoskeletal structures are input into the first neural network. The first neural network can then breakdown or filter the image data and compare the segmented musculoskeletal pixels to the trained anatomical co-variation model to identify and label neurological structure pixels corresponding to the segmented musculoskeletal pixels. The first neural network can then output an image volume with the now classified corresponding neurological structures overlaid on the previously-classified musculoskeletal pixels of the CT or CBCT input volumes. This can be seen in FIG. 13, where an input image volume 1322 has segmented musculoskeletal tissue. The first U-Net 1320 can receive the input 1322 and produce an output 1332 with labeled corresponding neurological structures. The Transitioning now to deployment of an image analysis tool of the present invention, in step 1450, a second predictive model can be used to generate and learn associations between raw image volumes and corresponding neurological structures. The second predictive model can preferably be a second neural network, and preferably a second U-Net. The second predictive model can be configured as an automated gray-level labeler. One having ordinary skill in the art will recognize that the second predictive model is not limited to generating and labeling CBCT volumes from gray-level CBCT data. Rather, the second predictive model of the present invention can take as an input any known unlabeled image format and generate and label anatomical structures present in the imaged volume using the systems and methods disclosed herein, so long as a first neural network, or first U-Net, of the present invention was trained on the same type of image format.

With reference to FIG. 13, a second predictive model or second U-Net 1350, is schematically illustrated. The second predictive model or U-Net can receive an unlabeled image volume 1352 as an input. The unlabeled image volume can be a gray-level CBCT scan, an unlabeled CT scan, etc. The second predictive model 1350 can use a ground truth pixel label classification generated from the predictions and inputs of the first predictive model or U-Net 1320. In other words, the second predictive model can receive unlabeled image volumes and use the trained first predictive model to analyze the unlabeled image volumes to classify pixels associated with neurological structures present in the imaged anatomical region. Additionally or alternatively, the second predictive model or second U-Net can also identify and label musculoskeletal structures of the unlabeled input volumes.

Finally, in step 1460, an output of the second predictive model can be converted into a surface model for analysis and use. A converted output of the second predictive model can be seen in FIG. 13, as an automatically segmented volume output 1362. The second predictive model can segment both neurological structures and musculoskeletal structures. For example, as shown in FIG. 13, the second U-Net 1350 can automatically identify and model first and second psoas muscles 1364, 1368, first and second vertebral bodies 1370, 1372, and first and second neurological structures 1374, 1376. In one embodiment, a segmentation to surface model conversion algorithm, such as, for example, marching cubes, can be used to convert the second predictive model output into a surface model. As discussed above, the surface model can be used in many different ways. For example, the surface model output of an image analysis tool of the present invention, and, more particularly, of a second predictive model can be used in conjunction with a computer assisted navigation environment or a robotic surgical system. Alternatively, the surface model with identified neurological structures can be used by a surgeon in pre-operative planning.

In some embodiments, a displayed labeled image volume updates in accordance with intra-operative feedback on a location of at least one neurological structure.

In some embodiments, a surgical instrument may be used to provide the intra-operative feedback on the location of the at least one neurological structure.

In some embodiments, the surgical instrument is one of an auxiliary nerve localization system, a computer aided navigation system, a monitoring probe, or a camera.

In some embodiments, an intra-operative CT or CBCT patient scan may be performed to provide the intra-operative feedback on the location of the at least one neurological structure.

In some embodiments, the patient-specific surgical plan may be inputted into a robotic surgical system.

In some embodiments, a safe access zone may be identified around the identified at least one neurological structure.

In some embodiments, the image analysis tool identifies the at least one neurological structure based on a predictive model and patient phenotype information.

In some embodiments, a method of training an image analysis tool to identify at least one neurological structure from an unsegmented image for use in a surgical procedure may comprise: annotating a first training dataset to identify musculoskeletal structure and neurological structure; inputting the first training dataset into a first neural network to train an anatomical covariation model; annotating a second training dataset to identify musculoskeletal structure; and inputting the second training dataset into the first neural network such that the first neural network outputs at least one neurological structure corresponding to the identified musculoskeletal structure of the second training dataset.

In some embodiments, the first training dataset comprises at least one high quality MRI volume and the second training dataset comprises at least one CT or CBCT volume.

In some embodiments, the at least one CT or CBCT volume includes the same musculoskeletal structure as the at least one high quality MRI volume.

In some embodiments, a transformation on the first training dataset may be performed to generate an additional training dataset; the additional training dataset may be annotated to identify musculoskeletal structure and neurological structure; and the additional training dataset may be inputted into the first neural network to train the anatomical covariation model.

In some embodiments, a method of performing a minimally invasive surgical procedure may comprise: acquiring an unsegmented patient scan of a surgical region; identifying neurological structures in the surgical region from the unsegmented scan using an image analysis tool; creating a patient-specific surgical access plan using the identified neurological structures; and performing a surgical access procedure in accordance with the patient-specific access plan.

In some embodiments, intra-operative feedback may be received from at least one surgical instrument regarding positioning of the identified neurological structures; and the patient-specific surgical access plan may be updated.

In some embodiments, real-time positioning of at least one of the identified neurological structures, a surgical instrument, and a patient position may be displayed.

Referring now to FIGS. 18-22 generally, the terms artificial neural network (ANN) and neural network may be used interchangeably herein. An ANN may be configured to determine a classification (e.g., type of object) based on input image(s) or other sensed information. An ANN is a network or circuit of artificial neurons or nodes, and it may be used for predictive modeling.

The prediction models may be and/or include one or more neural networks (e.g., deep neural networks, artificial neural networks, or other neural networks), other machine learning models, or other prediction models.

Disclosed implementations of artificial neural networks may apply a weight and transform the input data by applying a function, this transformation being a neural layer. The function may be linear or, more preferably, a nonlinear activation function, such as a logistic sigmoid, Tanh, or ReLU function. Intermediate outputs of one layer may be used as the input into a next layer. The neural network through repeated transformations learns multiple layers that may be combined into a final layer that makes predictions. This learning (i.e., training) may be performed by varying weights or parameters to minimize the difference between the predictions and expected values. In some embodiments, information may be fed forward from one layer to the next. In these or other embodiments, the neural network may have memory or feedback loops that form, e.g., a neural network. Some embodiments may cause parameters to be adjusted, e.g., via back-propagation.

An ANN is characterized by features of its model, the features including an activation function, a loss or cost function, a learning algorithm, an optimization algorithm, and so forth. The structure of an ANN may be determined by a number of factors, including the number of hidden layers, the number of hidden nodes included in each hidden layer, input feature vectors, target feature vectors, and so forth. Hyperparameters may include various parameters which need to be initially set for learning, much like the initial values of model parameters. The model parameters may include various parameters sought to be determined through learning. And the hyperparameters are set before learning, and model parameters can be set through learning to specify the architecture of the ANN.

Learning rate and accuracy of an ANN rely not only on the structure and learning optimization algorithms of the ANN but also on the hyperparameters thereof. Therefore, in order to obtain a good learning model, it is important to choose a proper structure and learning algorithms for the ANN, but also to choose proper hyperparameters.

The hyperparameters may include initial values of weights and biases between nodes, mini-batch size, iteration number, learning rate, and so forth. Furthermore, the model parameters may include a weight between nodes, a bias between nodes, and so forth.

In general, the ANN is first trained by experimentally setting hyperparameters to various values, and based on the results of training, the hyperparameters can be set to optimal values that provide a stable learning rate and accuracy.

Figure 18:
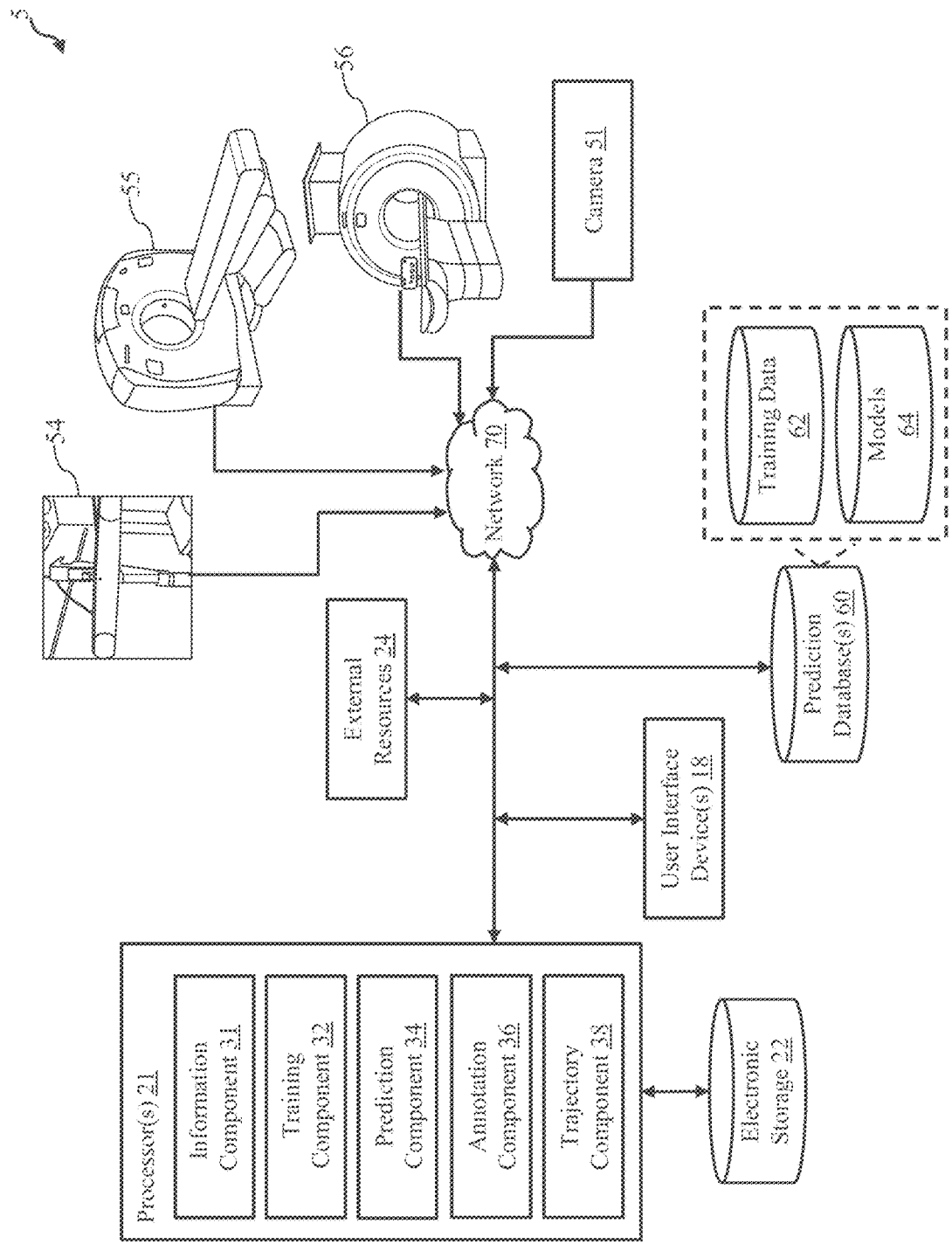
FIG. 18 illustrates an example of a system in which MISS is assisted, in accordance with one or more embodiments.

Some embodiments of models 64 in system 5 depicted in FIG. 18 may comprise a CNN. A CNN may comprise an input and an output layer, as well as multiple hidden layers. The hidden layers of a CNN typically comprise a series of convolutional layers that convolve with a multiplication or other dot product. The activation function is commonly a ReLU layer, and is subsequently followed by additional convolutions such as pooling layers, fully connected layers and normalization layers, referred to as hidden layers because their inputs and outputs are masked by the activation function and final convolution.

The CNN computes an output value by applying a specific function to the input values coming from the receptive field in the previous layer. The function that is applied to the input values is determined by a vector of weights and a bias (typically real numbers). Learning, in a neural network, progresses by making iterative adjustments to these biases and weights. The vector of weights and the bias are called filters and represent particular features of the input (e.g., a particular shape).

In some embodiments, the learning of models 64 may be of reinforcement, supervised, semi-supervised, and/or unsupervised type. For example, there may be a model for certain predictions that is learned with one of these types but another model for other predictions may be learned with another of these types.

Supervised learning is the machine learning task of learning a function that maps an input to an output based on example input-output pairs. It may infer a function from labeled training data comprising a set of training examples. In supervised learning, each example is a pair consisting of an input object (typically a vector) and a desired output value (the supervisory signal). A supervised learning algorithm analyzes the training data and produces an inferred function, which can be used for mapping new examples. And the algorithm may correctly determine the class labels for unseen instances.

Unsupervised learning is a type of machine learning that looks for previously undetected patterns in a dataset with no pre-existing labels. In contrast to supervised learning that usually makes use of human-labeled data, unsupervised learning does not via principal component (e.g., to preprocess and reduce the dimensionality of high-dimensional datasets while preserving the original structure and relationships inherent to the original dataset) and cluster analysis (e.g., which identifies commonalities in the data and reacts based on the presence or absence of such commonalities in each new piece of data).

Semi-supervised learning makes use of supervised and unsupervised techniques.

Models 64 may analyze made predictions against a reference set of data called the validation set. In some use cases, the reference outputs resulting from the assessment of made predictions against a validation set may be provided as an input to the prediction models, which the prediction model may utilize to determine whether its predictions are accurate, to determine the level of accuracy or completeness with respect to the validation set data, or to make other determinations. Such determinations may be utilized by the prediction models to improve the accuracy or completeness of their predictions. In another use case, accuracy or completeness indications with respect to the prediction models' predictions may be provided to the prediction model, which, in turn, may utilize the accuracy or completeness indications to improve the accuracy or completeness of its predictions with respect to input data. For example, a labeled training dataset may enable model improvement. That is, the training model may use a validation set of data to iterate over model parameters until the point where it arrives at a final set of parameters/weights to use in the model.

In some embodiments, training component 32 depicted in FIG. 18 may implement an algorithm for building and training one or more deep neural networks. A used model may follow this algorithm and already be trained on data. In some embodiments, training component 32 may train a deep learning model on training data 62 depicted in FIG. 18 providing even more accuracy, after successful tests with these or other algorithms are performed and after the model is provided a large enough dataset.

A model implementing a neural network may be trained using training data of storage/database 62. The training data may include many anatomical attributes. For example, this training data obtained from prediction database 60 of FIG. 18 may comprise hundreds, thousands, or even many millions of pieces of information (e.g., images, scans, or other sensed data) describing portions of a cadaver or live body, to provide sufficient representation of a population or other grouping of patients. The dataset may be split between training, validation, and test sets in any suitable fashion. For example, some embodiments may use about 60% or 80% of the images or scans for training or validation, and the other about 40% or 20% may be used for validation or testing. In another example, training component 32 may randomly split the labelled images, the exact ratio of training versus test data varying throughout. When a satisfactory model is found, training component 32 may train it on 95% of the training data and validate it further on the remaining 5%.

The validation set may be a subset of the training data, which is kept hidden from the model to test accuracy of the model. The test set may be a dataset, which is new to the model to test accuracy of the model. The training dataset used to train prediction models 64 may leverage, via training component 32, an SQL server and a Pivotal Greenplum database for data storage and extraction purposes.

In some embodiments, training component 32 may be configured to obtain training data from any suitable source, e.g., via prediction database 60, electronic storage 22, external resources 24 (e.g., which may include sensors, scanners, or another device), network 70, and/or UI device(s) 18. The training data may comprise captured images, smells, light/colors, shape sizes, noises or other sounds, and/or other discrete instances of sensed information.

In some embodiments, training component 32 may enable one or more prediction models to be trained. The training of the neural networks may be performed via several iterations. For each training iteration, a classification prediction (e.g., output of a layer) of the neural network(s) may be determined and compared to the corresponding, known classification. For example, sensed data known to capture a closed environment comprising dynamic and/or static objects may be input, during the training or validation, into the neural network to determine whether the prediction model may properly predict a path for the user to reach or avoid said objects. As such, the neural network is configured to receive at least a portion of the training data as an input feature space. Once trained, the model(s) may be stored in database/storage 64 of prediction database 60, as shown in FIG. 18, and then used to classify samples of images or scans based on visible attributes.

Electronic storage 22 of FIG. 18 comprises electronic storage media that electronically stores information. The electronic storage media of electronic storage 22 may comprise system storage that is provided integrally (i.e., substantially non-removable) with system 5 and/or removable storage that is removably connectable to system 5 via, for example, a port (e.g., a USB port, a firewire port, etc.) or a drive (e.g., a disk drive, etc.). Electronic storage 22 may be (in whole or in part) a separate component within system 5, or electronic storage 22 may be provided (in whole or in part) integrally with one or more other components of system 5 (e.g., a user interface (UI) device 18, processor 21, etc.). In some embodiments, electronic storage 22 may be located in a server together with processor 21, in a server that is part of external resources 24, in UI devices 18, and/or in other locations. Electronic storage 22 may comprise a memory controller and one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information obtained and/or determined by processor 21, information received via UI devices 18 and/or other external computing systems, information received from external resources 24, and/or other information that enables system 5 to function as described herein.

External resources 24 may include sources of information (e.g., databases, websites, etc.), external entities participating with system 5, one or more servers outside of system 5, a network, electronic storage, equipment related to Wi-Fi technology, equipment related to Bluetooth® technology, data entry devices, a power supply (e.g., battery powered or line-power connected, such as directly to 110 volts AC or indirectly via AC/DC conversion), a transmit/receive element (e.g., an antenna configured to transmit and/or receive wireless signals), a network interface controller (NIC), a display controller, a graphics processing unit (GPU), and/or other resources. In some implementations, some or all of the functionality attributed herein to external resources 24 may be provided by other components or resources included in system 5. Processor 21, external resources 24, UI device 18, electronic storage 22, a network, and/or other components of system 5 may be configured to communicate with each other via wired and/or wireless connections, such as a network (e.g., a local area network (LAN), the Internet, a wide area network (WAN), a radio access network (RAN), a public switched telephone network (PSTN), etc.), cellular technology (e.g., GSM, UMTS, LTE, 5G, etc.), Wi-Fi technology, another wireless communications link (e.g., radio frequency (RF), microwave, infrared (IR), ultraviolet (UV), visible light, cm wave, mm wave, etc.), a base station, and/or other resources.

UI device(s) 18 of system 5 may be configured to provide an interface between one or more users and system 5. UI devices 18 are configured to provide information to and/or receive information from the one or more users. UI devices 18 include a UI and/or other components. The UI may be and/or include a graphical UI configured to present views and/or fields configured to receive entry and/or selection with respect to particular functionality of system 5, and/or provide and/or receive other information. In some embodiments, the UI of UI devices 18 may include a plurality of separate interfaces associated with processors 21 and/or other components of system 5. Examples of interface devices suitable for inclusion in UI device 18 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that UI devices 18 include a removable storage interface. In this example, information may be loaded into UI devices 18 from removable storage (e.g., a smart card, a flash drive, a removable disk) that enables users to customize the implementation of UI devices 18.

In some embodiments, UI devices 18 are configured to provide a UI, processing capabilities, databases, and/or electronic storage to system 5. As such, UI devices 18 may include processors 21, electronic storage 22, external resources 24, and/or other components of system 5. In some embodiments, UI devices 18 are connected to a network (e.g., the Internet). In some embodiments, UI devices 18 do not include processor 21, electronic storage 22, external resources 24, and/or other components of system 5, but instead communicate with these components via dedicated lines, a bus, a switch, network, or other communication means. The communication may be wireless or wired. In some embodiments, UI devices 18 are laptops, desktop computers, smartphones, tablet computers, and/or other UI devices.

Data and content may be exchanged between the various components of the system 5 through a communication interface and communication paths using any one of a number of communications protocols. In one example, data may be exchanged employing a protocol used for communicating data across a packet-switched internetwork using, for example, the Internet Protocol Suite, also referred to as TCP/IP. The data and content may be delivered using datagrams (or packets) from the source host to the destination host solely based on their addresses. For this purpose the Internet Protocol (IP) defines addressing methods and structures for datagram encapsulation. Of course other protocols also may be used. Examples of an Internet protocol include Internet Protocol version 4 (IPv4) and Internet Protocol version 6 (IPv6).

In some embodiments, processor(s) 21 may form part (e.g., in a same or separate housing) of a user device, a consumer electronics device, a mobile phone, a smartphone, a personal data assistant, a digital tablet/pad computer, a wearable device (e.g., watch), AR goggles, VR goggles, a reflective display, a personal computer, a laptop computer, a notebook computer, a work station, a server, a high performance computer (HPC), a vehicle (e.g., embedded computer, such as in a dashboard or in front of a seated occupant of a car or plane), a game or entertainment system, a set-top-box, a monitor, a television (TV), a panel, a space craft, or any other device. In some embodiments, processor 21 is configured to provide information processing capabilities in system 5. Processor 21 may comprise one or more of a digital processor, an analog processor, a digital circuit designed to process information, an analog circuit designed to process information, a state machine, and/or other mechanisms for electronically processing information. Although processor 21 is shown in FIG. 18 as a single entity, this is for illustrative purposes only. In some embodiments, processor 21 may comprise a plurality of processing units. These processing units may be physically located within the same device (e.g., a server), or processor 21 may represent processing functionality of a plurality of devices operating in coordination (e.g., one or more servers, UI devices 18, devices that are part of external resources 24, electronic storage 22, and/or other devices).

As shown in FIG. 18, processor 21 is configured via machine-readable instructions to execute one or more computer program components. The computer program components may comprise one or more of information component 31, training component 32, prediction component 34, annotation component 36, trajectory component 38, and/or other components. Processor 21 may be configured to execute components 31, 32, 34, 36, and/or 38 by: software; hardware; firmware; some combination of software, hardware, and/or firmware; and/or other mechanisms for configuring processing capabilities on processor 21.

It should be appreciated that although components 31, 32, 34, 36, and 38 are illustrated in FIG. 18 as being co-located within a single processing unit, in embodiments in which processor 21 comprises multiple processing units, one or more of components 31, 32, 34, 36, and/or 38 may be located remotely from the other components. For example, in some embodiments, each of processor components 31, 32, 34, 36, and 38 may comprise a separate and distinct set of processors. The description of the functionality provided by the different components 31, 32, 34, 36, and/or 38 described below is for illustrative purposes, and is not intended to be limiting, as any of components 31, 32, 34, 36, and/or 38 may provide more or less functionality than is described. For example, one or more of components 31, 32, 34, 36, and/or 38 may be eliminated, and some or all of its functionality may be provided by other components 31, 32, 34, 36, and/or 38. As another example, processor 21 may be configured to execute one or more additional components that may perform some or all of the functionality attributed below to one of components 31, 32, 34, 36, and/or 38.

Figure 20A:
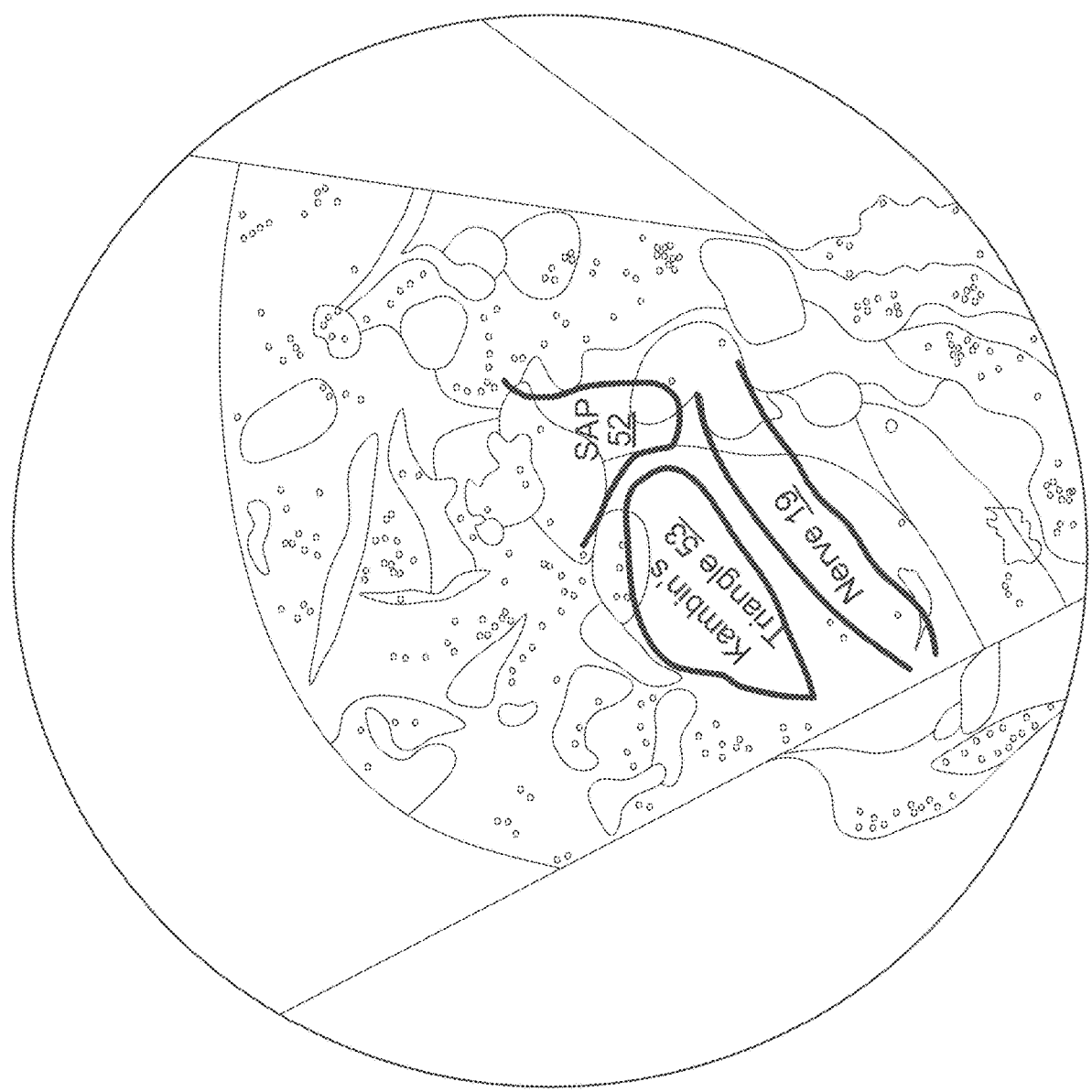

The disclosed approach relates to advanced imaging solutions and systems to augment camera images in real-time with clinically relevant information such as neural and bony structures. An output of system 5 may be a camera image that has overlaid in real-time relevant structures. The user may select what level of information/refinement may be required. The overlay may be performed based on confidence intervals of ROIs of anatomical structures. The confidence intervals may be determined based on information available prior to access and then updated to tighten estimated ROIs as new information becomes available intra-operation, e.g., as the camera is advanced in the port. FIG. 20A is an example output that would be displayed on a system monitor.

In some embodiments, the confidence interval may be similar to or the same as confidence interval 50 described above. And each one may encode how confident system 5 is that the anatomical structure is indeed what it is predicted to be. For example, annotation component 36 may overlay a transition zone or margin, or it may annotate a color-coded bullseye, where green indicates uppermost confidence. And, when annotating presence of Kambin's triangle 53 in a camera image, as the triangle's boundary extends outward it may become more red. The red portion may represent that, while still being near Kambin's triangle 53, there may be less confidence of that being the case. A same or similar approach may be performed when indicating a nerve root or other structure. For example, annotation component 36 may indicate where the center of the nerve is with 100% confidence; but the boundary may change in appearance, when extending outwards, indicating increased dubiousness.

Figure 19A:
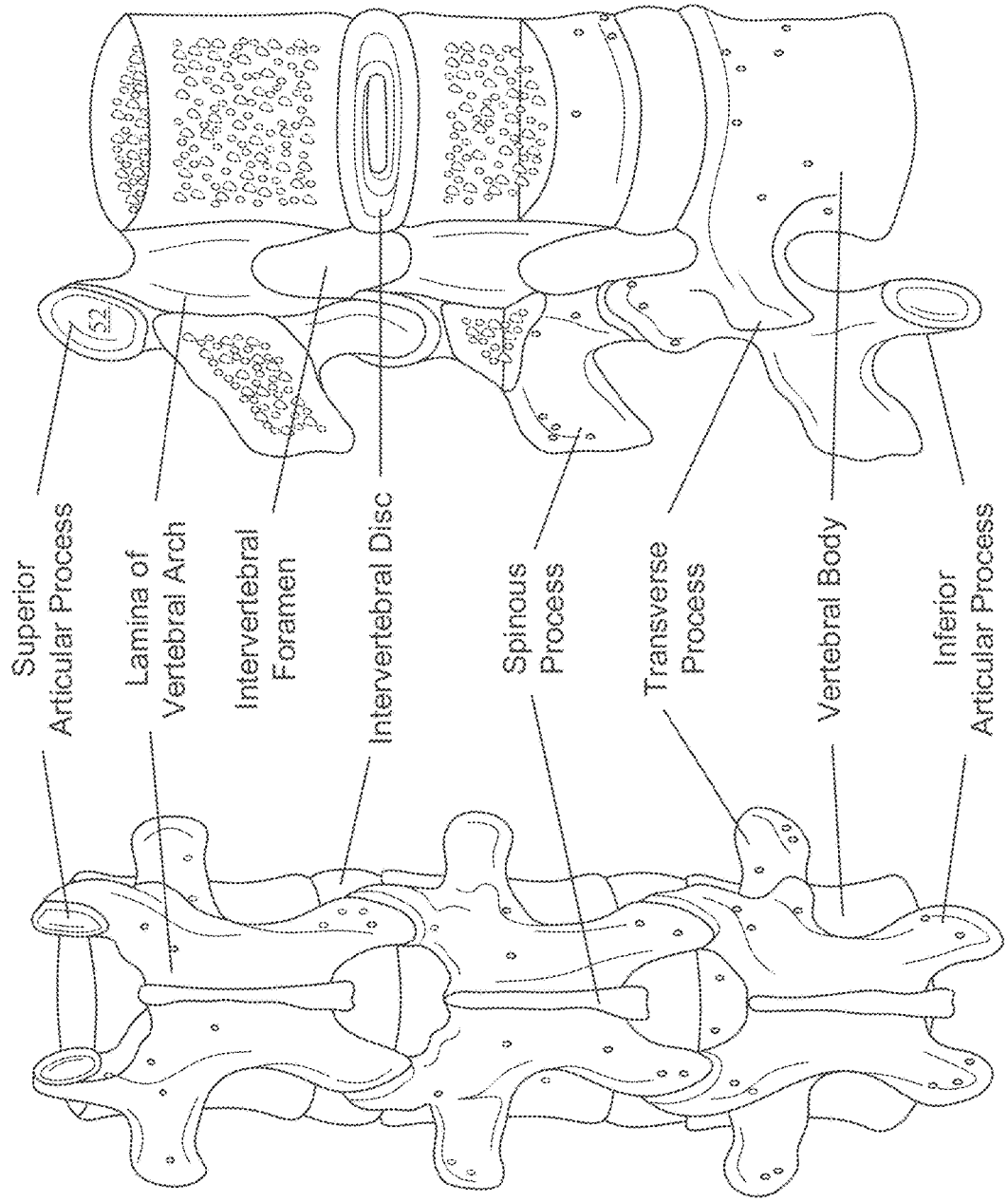
FIG. 19A comprises posterior and lateral elevational views of a portion of a vertebral column, in accordance with the prior art.
Figure 19B:
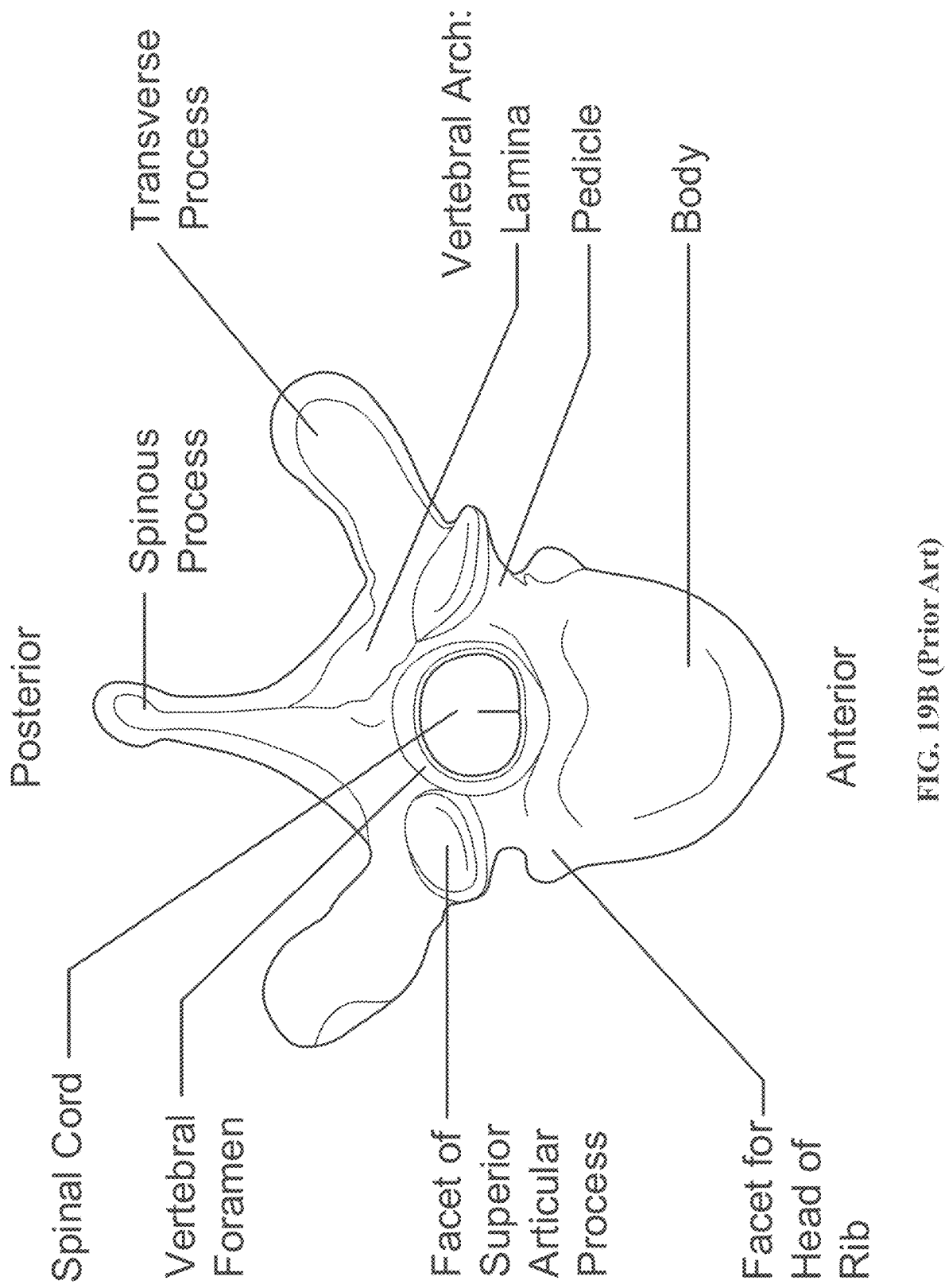
FIG. 19B comprises a superior view of a vertebra, in accordance with the prior art.

FIG. 19A is a lateral view of a vertebral column, the vertebral column comprising a series of vertebral bodies or alternative vertebrae and fibrous intervertebral discs that provide axial support and movement to the upper portions of the body. The vertebral column typically comprises thirty-three vertebrae 11, with seven cervical (C1-C7), twelve thoracic (T1-T12), five lumbar (L1-L5), five fused sacral (S1-S5), and four fused coccygeal vertebrae.

FIG. 20B is a schematic view of Kambin's triangle 53. Kambin's triangle 53 may be any polygon or shape (e.g., a triangle or only triangular by generalization or approximation). Kambin's triangle 53 may be the site of posterolateral access for spinal surgery. It can be defined as a right triangle over the intervertebral disc viewed dorsolaterally. The hypotenuse may be exiting nerve root 19, the base may be the superior border or endplate of the inferior vertebra, and the height may be traversing nerve root 23 or SAP 52. Intervertebral disc may be accessed through this region by performing a foraminoplasty in which a portion of the inferior vertebra is removed such that surgical instruments or implants can be introduced at this region of the spine. For example, system 5 may be used for accessing Kambin's triangle 53 and implanting an expandable implant therethrough. In such a procedure, it is often desired to protect exiting nerve root 19 and traversing nerve root 23.

The intervertebral disc may be accessed through Kambin's triangle 53, e.g., by performing endoscopic foraminoplasty while protecting the nerve. Utilizing foraminoplasty to access the intervertebral disc through Kambin's triangle 53 can have several advantages (e.g., less or reduced trauma to the patient) as compared to accessing the intervertebral disc posteriorly or anteriorly as is typically done in the art. In particular, surgical procedures involving posterior access often require removal of the facet joint. For example, TLIF typically involves removal of one facet joint to create an expanded access path to the intervertebral disc. Removal of the facet joint can be very painful for the patient, and is associated with increased recovery time. In contrast, accessing the intervertebral disc through Kambin's triangle 53 may advantageously avoid the need to remove the facet joint.

Endoscopic foraminoplasty may provide for expanded access to the intervertebral disc without removal of a facet joint. Sparing the facet joint may reduce patient pain and blood loss associated with the surgical procedure. In addition, sparing the facet joint can advantageously permit the use of certain posterior fixation devices which utilize the facet joint for support (e.g., trans-facet screws, trans-pedicle screws, and/or pedicle screws). In this manner, such posterior fixation devices can be used in combination with interbody devices inserted through Kambin's triangle 53.

In an example lumbar spine, the thecal sac may be round. In some patients, the thecal sac may form the vertical side of Kambin's triangle 53, e.g., where the superior articular process may be. And the superior endplate vertebrae may form the horizontal side or base of said triangle. The thecal sac may be filled with the cerebrospinal fluid in which the spinal cord and the cauda equina roots and some free subarachnoid blood vessels float freely.

A vertebral end plate may be the transition region where a vertebral body and intervertebral disc interface with each other. The portion of Kambin's triangle 53 forming a right angle may be the border of foraminoplasty (e.g., where SAP 52 may be).

In some embodiments, annotation component 36 may indicate each pixel of a captured image as to whether it represents a nerve, Kambin's triangle, or other structure(s). For example, prediction component 34 may indicate that there is a 90% probability that a pixel represents Kambin's triangle 53 and a 60% probability that the pixel represents nerve root 19. In this example, annotation component 36 may then take a maximum of these two probabilities, when determining to annotate that pixel or region positively as Kambin's triangle. Alternatively, there may be a color code that blends colors (e.g., red and green) to visually represent a level of confidence that the prediction is accurate. Irrespective of this annotation approach, the representations may be updated in real-time upon obtaining access and when advancing camera 51 therein.

In some embodiments, models 64 may be a single CNN or another neural network that outputs all three of: (i) vertebral bodies and foramen, (ii) nerve roots, and (iii) bony landmarks. In other embodiments, there may be three networks, each of which outputting one of those three different types of anatomical structures. Accordingly, semantic segmentation is a contemplated approach. A class probability may be predicted for each structure of said three different types. For each pixel there may be a probability, e.g., where it is 80% Kambin's triangle 53, 10% superior articular process (SAP) 52, and 10% exiting nerve root 19, and then the annotation would indicate Kambin's triangle. The detections can be further enhanced by leveraging shape priors, for instance, pixels representing the Kambin's triangle can be grouped to resemble a triangle.

In some implementations, pre-op scans from CT 55 and/or MRI 56 depicted in FIG. 18 may have been taken some time beforehand (e.g., a month), which may be significant as the ROI may have already changed and/or the patient position during surgery may be different than from during the scans, rendering the scans somewhat outdated. And then, when a tool and/or medical practitioner accesses the scene, the ROI becomes manipulated. Image(s) captured from camera 51 may thus serve as an anchor of what is actually at the ROI, as opposed to the CT and/or MRI scans merely showing what is to be expected there.

In some embodiments, prediction component 34 may adapt predictions based on a patient, e.g., by predicting with just the CT scan and then adjusting the prediction or re-predicting based on images captured from camera 51 in real-time. As such, these images may be used together with previously taken scans of a patient. For example, the scan from CT 55 may help determine the ROI; and then, when starting to use camera 51, a prediction of a location of Kambin's triangle 53 may be updated in real-time. In this or another example, the orientation may change. With such pre-operation scans there may be more information that can be leveraged to identify Kambin's triangle 53 and/or to adjust a trajectory of an advancing instrument on which camera 51 and/or an implant may be mounted.

In some embodiments, trajectory component 38 may determine whether a trajectory of the advancement satisfies a criterion. And then this component may adjust the trajectory such that the criterion is satisfied, in response to the determination that the trajectory did not satisfy the criterion.

Although herein contemplated are embodiments that recognize or detect anatomical structures from only camera images, the CT and/or MRI scans help (e.g., with relative orientation and sizes) by providing more information that may be used to enhance accuracy of said recognition or detection. For example, nerve roots 19, 23 may be identified using an MRI scan that corresponds to a captured image, model 64 being trained with training data comprising ground truth labeled based on nerve root structures identified in previously-taken MRI scans.

In a first set of embodiments, prediction component 34 may predict presence of one or more anatomical structures (e.g., Kambin's triangle, neural structure, and/or a bony structure) using only camera 51 and a CNN or U-Net. In a second set of embodiments, a prediction of anatomical structures may be performed using at least one pre-operation scan from at least one of MRI 56 and CT 55. And, in a third set of embodiments with a navigated camera, the prediction may be performed using an output from a two-dimensional (2D) CT (e.g., C-Arm 54). In the third set of embodiments, prediction component 34 may use 2D to 3D image reconstruction to identify Kambin's triangle and/or bony landmarks. Annotation component 36 may then overlay a representation of the identification(s) on the camera image. As such, calibration targets or a navigated C-arm may be used to predict Kambin's triangle based on atlas or statistical shape models depending on patient phenotype.

In one or more of these embodiments, an expert or surgeon with prior knowledge may annotate or label images of training data beforehand (e.g., which surgeons already built indicating location of anatomical structures) and directly learn, e.g., from a statistical set of other samples to then build upon it. The annotated images may be with various levels of tissue penetration or bioavailability. Upon being trained, models 64 of these embodiments may be used to predict presence of these structures in captured images, each with corresponding confidence intervals around these structures. As more images are available during access, bounds of these structures may tighten.

In some embodiments, trajectory component 38 may use the camera images and various landmarks to provide orientation information and correction (e.g., when non-navigated). For example, if the camera orientation is changed during the medical procedure, this component may keep the same field of view by analyzing the rotation of landmarks of the image and maintaining a constant pose. As the camera turns, prediction component 34 may detect the structures somewhere else; then, trajectory component 38 may deduce how much camera 51 was turned to keep that pose. In embodiments where the camera is navigated, then trajectory component 38 may already know how much of the scene was rotated to perform a suitable correction.

In some embodiments, information component 31 may store information about how the ROI was accessed to then learn from that (e.g., as model parameters or for hyperparameter tuning). In these or other embodiments, 3D CT scans may enable use of prior bony anatomy information to perform training of models 64. The CNNs implemented by models 64 may perform segmentation. This segmentation may be of spine structures via the CT scan. The segmentation helps with detection of these structures, e.g., when Kambin's triangle 53 is suspected to be below or above a particular structure. As such, context of what is in the image of camera 51 may be determined, increasing probability of an improved detection of said triangle.

In some embodiments, patient demographic information (e.g., size, weight, gender, bone health, or another attribute) and what level may be of the lumbar (e.g., L1, L2 versus L4, L5) may be obtained via training component 32 and/or prediction component 34. These attributes may serve as model parameters or in hyperparameter tuning, to help improve performance.

As mentioned, some embodiments of a CNN of model 64 may have as input (i.e., for training and when in deployment) just camera images, e.g., with surgeons performing the ground truth annotations. But other embodiments may have camera images, some high-level information, and CT scans (and even potentially further using MRI scans) for said input, e.g., using the 3D CT scan segmentation results as ground truth. The overlaid outputs (e.g., as shown in FIG. 20A), from these embodiments, may be similar, but with the latter, other embodiments having more accurate predictions without requiring surgeons anymore for labeling due to having the segmentation information. In other words, the CT scan may be good enough to automatically detect, via a CNN, Kambin's triangle 53, to then transfer that learning to the CNN using camera images.

In some embodiments, annotations for the learning performed using CT scans may be supervised, unsupervised, or semi-supervised.

In some embodiments, annotation component 36 may provide a medical practitioner with a UI that indicates where anatomical structures are located (e.g., in the region displayed in the example of FIG. 20A or another ROI) based on a set (e.g., one or more) of images from camera 51, e.g., taken during an approach to Kambin's triangle 53. In these or other embodiments, trajectory component 38 may determine (e.g., for informing the medical practitioner) what changes need to be made in a trajectory; as a result, an improved trajectory towards Kambin's triangle 53 may be achieved. In either embodiments, the disclosed implementation of artificial intelligence may improve efficiency and safety of surgical equipment via improved accuracy in identifying Kambin's triangle 53. For example, needless and erroneous movements of a surgical instrument, which endanger a patient (e.g., when contacting a nerve) may be avoided.

In some embodiments, trajectory component 38 may determine and continually update a current distance from a device that captured the image to the identified triangle. In these or other embodiments, trajectory component 38 may determine a position of a dilator advancing towards the identified triangle. The image may be captured via at least one of a camera, charge coupled device (CCD), and optical sensor mounted on a side of the dilator.

In some embodiments, annotation component 36 may indicate in near real-time at least one of Kambin's triangle 53, SAP 52, and nerve 19. As shown in the example of FIG. 20A, the boundaries may be indicated with thicker lines on the camera image, and text indicating each of these structures may be annotated thereon as well. Alternatively, pixels or other marks may be used to differentiate the structure. A user may, via UI devices 18, select what should be emphasized and how such representative emphasis should be performed. For example, such user-configurable annotating may make the SAP boundary (or boundary of the nerve or Kambin's triangle) and/or corresponding text optional.

In some embodiments, trajectory component 38 may identify a way of advancing a tool towards or through Kambin's triangle 53, without touching a nerve, based on a relative location of SAP 52, superior endplate vertebrae, and/or another structure in the ROI that may act as an anatomical landmark. From a CT scan, presence of SAP 52, levels of the spinal cord, and/or other bony landmarks may be predicted, each of which being predicted at a set of particular locations. And, from an MRI scan, nerve roots 19, 23 may be predicted as being present at particular locations. To identify Kambin's triangle 53, the presence of three edges may be predicted, e.g., including nerve 19, SAP 52, and the superior endplate vertebrae.

In some embodiments, camera 51 may perform hyper-spectral or multi-spectral imaging (i.e., for wavelengths other than just white light) for visually obtaining information on blood supply, arteries, nerves, and the like. Overlaying information about these other wavelengths may also be optional for a user.

In some embodiments, trajectory component 38 may identify the position of the dilators as they advance toward Kambin's triangle 53, and based on those images give the medical practitioner feedback. Herein, a medical practitioner may refer to human-based surgery, a combination of computer usage and human surgery, or pure automation.

In some embodiments, camera 51 may be mounted at a tip of a retractor (e.g., Fox telogen or another instrument), for identifying or finding anatomical structures, including Kambin's triangle 53 and a nerve.

In some embodiments, camera 51 may be mounted or integrated on an access tube, which is a retractor. And at the tip of it there may be irrigation suction so that working space is not used when inserting another endoscope or another instrument. As such, camera 51 may be built into the port itself. Demonstrable with respect to FIG. 20A, camera 51 may already be on the retractor fixture and embedded on its side. In FIG. 20A, the camera is located at the bottom-middle and looking upwards.

In an implementation, dilators and the access cannula may get inserted up to Kambin's triangle 53, but they may not go through it. A disc cleaner may go through there and then clean the disc. One or more aspects thereof or other structure of the probe may dock on bones around the dilator port or Kambin's triangle 53.

In some embodiments, camera 51 may be navigated (e.g., the CT scan and port/camera being registered). For example, navigation of the camera may be tracked in real-time, for knowing in space where the port is. That is, this may be registered to the pre-operation image to know where everything is relative to each other and to know from where the viewpoint is. As mentioned, camera 51 may be on the side of the port or on the side of the dilator. This may be compensated for, knowing that the working channel is going to be then offset from the camera (e.g., by a few millimeters). For example, these may be about 30 degrees. There may be 0 and 30 degree endoscopes, with the 30 degree ones showing around a corner.

When looking ahead, there may be some distortion that may be corrected, when knowing exactly what that angle is and some good idea of the working distance. Accordingly, the image that is provided from camera 51 may be based on the camera location being skewed so that the center of the image is actually through the working channel; and there may be some software corrections performed via an imaging processing pipeline. In some implementations, when looking from the side, a user may get a lot more distortion on the top (e.g., upper portion of FIG. 20A) the further away the camera is, with the angle. But a majority of this may be corrected. When corrected, it may look all centered to the user. When not corrected, there may be a lens effect due to being off the center. This may not cause a loss of information, there being rather just different pixels representing a different area. This is known as fisheye distortion and may be corrected.

In implementations comprising CT 55, a patient may be laying on a table when scanned. Then, a number or days or weeks later, come surgery time, they may be laying at a different position when putting in camera 51. For example, a little device may be put in nearby and then screw in at the lumbar region (e.g., L5-S1 area). A quick CT scan may be performed, and then the inserted instrument may have a reflector that pops up in the CT scan; there may also be a camera in the operating room that knows exactly where that instrument is in space. Accordingly, the patient, images, or devices may be registered, e.g., by aligning the camera's image with the coordinate system from the previously taken scans. The registration may further be performed with a scanner and a reference array or markers. The flexible nature of the spine can increase the risk of movement and thereby inaccuracies, making navigation significant for improving accuracy.

In embodiments where camera 51 is navigated and when 3D CT scans are used, prediction component 34 may automatically segment the CT scan (e.g., using deep learning) to identify vertebral bodies and foramen; a foramen is an open hole that exists in the body of animals to allow muscles, nerves, arteries, veins, or other structures to connect one part of the body with another. From these identifications, prediction component 34 may deduce Kambin's triangle 53. A representation of Kambin's triangle may then be overlaid on the image of camera 51. In these or other embodiments, prediction component 34 may automatically segment the CT scan (e.g., using deep learning trained through co-acquired MRI CT scans) to identify exiting nerve root 19. Annotation component 36 may then overlay this neural structure on the image. In these or other embodiments, prediction component 34 may automatically segment the CT scan (e.g., using deep learning) to identify such bony landmarks as the vertebra, pedicle, transverse process (TP), spinous process (SP), and/or SAP 52. Then, annotation component 36 may overlay the bony structures on the camera's image. As such, annotation component 36 may simultaneously overlay at least one of Kambin's triangle 53, neural structures 19, 23, and bony structures 52 on the image, with options for the user to refine an amount of information displayed.

In some embodiments, a machine learning model may be inputted 3D scans to predict where Kambin's triangle 53 is in each one (via supervised or unsupervised learning); and then another machine learning model may be trained using labels based on these predictions such that this other model makes predictions of Kambin's triangle using an image of a 2D camera. In other embodiments, human labeling of Kambin's triangle may be used for training a machine learning model; and then both the 2D camera and the 3D scans may be input into this model for predicting said triangle in real-time of a current patient. These embodiments implement distillation learning or student-teacher models.

In some embodiments, camera 51 may be non-navigated, even though 3D CT scans may be available. For example, deep learning may be performed to identify various bony landmarks directly from the 2D camera image as the intra-operation images of camera 51 are fed into this prediction model in real-time. In other embodiments, a user may have to wait some time (e.g., 10 seconds) to obtain a prediction of an identification of Kambin's triangle 53; nothing may move during that time period. The predictions may not be as fast as the camera feed itself, in some implementations, but it can update itself in near real-time as things move. For example, the port may be rotated (or a tool moved) to look from a particular angle.

When not navigated, a registration with a 3D CT scan may be performed in real-time based on landmarks that are found. Then, a confidence interval of Kambin's triangle, neural structures, and bony structures may be overlaid on the camera image. Due to the registration not being performed, a user may not know where the camera is looking versus where the CT scanner is looking. When navigated and registered, the user would know exactly where a 2D slice of the camera image is looking within the 3D CT scan. When not using a navigated camera, a user may know how a patient's bony anatomy looks, but they would have no way to link that to the camera image. This non-navigated approach may thus involve obtaining a prediction of the bones from the camera image and then registering that back to the 3D CT scan, which can be used to also predict presence of the bones to then estimate which 2D slice at which the user is looking.

In some embodiments, CT 55 is an XT (cone beam CT). In other embodiments where there is no CT scan available, then prediction component 34 may have to rely on some visual one unless a nerve locator device or some other means, such as an ultrasound or Sentio, is used to provide further imaging input to overlay on the camera image. In an example, an integrated device may be used to send an electric current through a probe or port to obtain information as to how close the device is to a nerve.

Figure 21:
FIG. 21 illustrates a process for improving accuracy of a medical procedure, in accordance with one or more embodiments.
Figure 22:
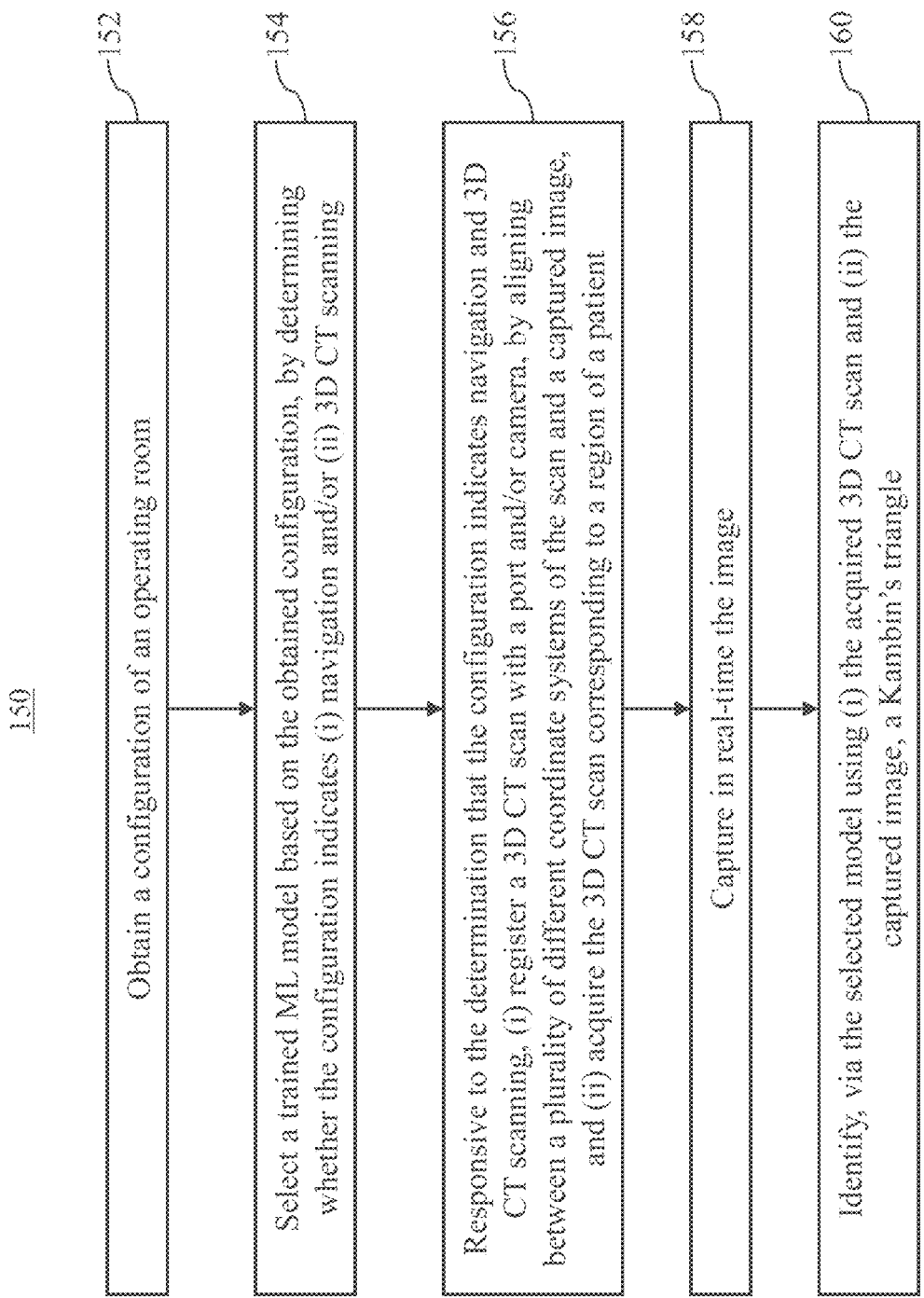
FIG. 22 illustrates a process for facilitating a situationally aware medical procedure, in accordance with one or more embodiments.

FIGS. 21-22 illustrate methods 100 and 150 for conducting accurate surgery with enhanced imaging, in accordance with one or more embodiments. These methods may be performed with a computer system comprising one or more computer processors and/or other components. The processors are configured by machine readable instructions to execute computer program components. The operations of these methods, which are presented below, are intended to be illustrative. In some embodiments, methods 100 and 150 may each be accomplished with one or more additional operations not described, and/or without one or more of the operations discussed. Additionally, the order in which the operations of each of these methods are illustrated in FIGS. 21-22. In some embodiments, each of methods 100 and 150 may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of these methods in response to instructions stored electronically on an electronic storage medium. The processing devices may include one or more devices configured through hardware, firmware, and/or software to be specifically designed for execution of one or more of these operations.

At operation 102 of method 100, one or more scans corresponding to an ROI of a patient may be acquired. For example, obtained patient scans may be unsegmented and correspond to a surgical region or a planned surgical region. In some embodiments, operation 102 is performed by a processor component the same as or similar to information component 31 and C-Arm 54, CT 55, and/or MRI 56 (shown in FIG. 18 and described herein).

At operation 104 of method 100, an image in the ROI of the patient may be captured in real-time. For example, camera 51 may take a set of images internal to the body or patient in real-time, the capturing of the set of images being performed during the procedure. Method 100 may be executed using one or more images at a time. In some embodiments, operation 104 is performed by a processor component the same as or similar to information component 31 and camera 51 (shown in FIG. 18 and described herein).

At operation 106 of method 100, training data may be obtained, the training data comprising ground truth labeled based on structures identified in previously-taken scans and corresponding images captured in real-time during a previous, medical procedure. In some embodiments, operation 106 is performed by a processor component the same as or similar to training component 32 (shown in FIG. 18 and described herein).

At operation 108 of method 100, the model may be trained with the obtained training data. For example, a trained CNN or another of models 64 may be obtained for performing recognition or detection of anatomical structures in the images and/or scans. That is, after training component 32 trains the neural networks, the resulting trained models may be stored in models 64 of prediction database 60. In some embodiments, operation 108 is performed by a processor component the same as or similar to training component 32.

At operation 110 of method 100, a plurality of different structures in, near, and/or around the ROI may be selected (e.g., manually via UI devices 18 or automatically based on a predetermined configuration) from among vertebral bodies and foramen, nerve roots, and bony landmarks. In some embodiments, operation 110 is performed by a processor component the same as or similar to information component 31 (shown in FIG. 18 and described herein).

At operation 112 of method 100, a Kambin's triangle and/or each selected structure may be identified, via a trained ML model using the acquired scan(s) and the captured image; each of the identifications may satisfy a confidence criterion, the identification of Kambin's triangle being based on a relative location of the selected structures. For example, the predicting is performed by identifying presence of at least one neurological structure from the unsegmented scan using an image analysis tool that receives as an input the unsegmented scan and outputs a labeled image volume identifying the at least one neurological structure. In some embodiments, prediction component 34 may predict via a U-Net, which may comprise a CNN developed for biomedical image segmentation and/or a fully convolutional network. In some embodiments, operation 112 is performed by a processor component the same as or similar to prediction component 34 (shown in FIG. 18 and described herein).

At operation 114 of method 100, representations of the identified triangle and/or of each selected structure may be overlaid, on the captured image. For example, information distinguishing, emphasizing, highlighting, or otherwise indicating anatomical structures may overlay the images, on a path of approach to Kambin's triangle 53. In some embodiments, operation 114 is performed by a processor component the same as or similar to annotation component 36 (shown in FIG. 18 and described herein).

At operation 116 of method 100, another image in the ROI of the patient may be subsequently captured in real-time. In some embodiments, operation 116 is performed by a processor component the same as or similar to information component 31 and camera 51.

At operation 118 of method 100, the Kambin's triangle may be re-identified, via the trained model using the acquired scan(s) and the other image. For example, a subsequent identification of Kambin's triangle 53 may satisfy an improved confidence criterion, e.g., for growing a region that represents the identified triangle based on a subsequently captured image. In some embodiments, operation 118 is performed by a processor component the same as or similar to prediction component 34.

At operation 120 of method 100, a confidence criterion associated with the re-identified triangle may be updated. For example, a confidence interval may be updated in real-time based on a feed of camera 51. In some embodiments, annotation component 36 may determine a confidence interval, e.g., while camera 52 is in proximity to the ROI and/or Kambin's triangle 53. The confidence interval may indicate an extent to which an anatomical structure is predicted to be present at each of a set of locations (e.g., 2D, 3D, or another suitable number dimensions). In some embodiments, a confidence criterion may be satisfied by an extent that improves upon known means, a higher assurance being obtained that Kambin's triangle 53 is indeed at the predicted location (e.g., for advancing towards said triangle). In some embodiments, operation 120 is performed by a processor component the same as or similar to prediction component 34 or annotation component 36.

At operation 122 of method 100, an updated representation of the re-identified triangle may be overlaid, on the other image. For example, the overlaying may be on a same or different image from the one used to make the prediction. In some embodiments, operation 122 is performed by a processor component the same as or similar to annotation component 36.

At operation 152 of method 150 as depicted in FIG. 22, a configuration of an operating room may be obtained. For example, whether an output from a 2D CT, 3D CT, and an MRI are available may be determined. In this or another example, whether camera 51 is navigable or registrable may be determined. In implementations where only CT scans are available of a patient, training component 32 may use MRI scans of other patients to train a method that can detect the nerves from the CT scan, as discussed herein. As such, by knowing where certain bony structures or landmarks are, prediction component 34 may predict where the nerve is. The algorithmic approach may itself be determined based on availability of specific tools and technologies. For example, system 5 may thus use certain inputs and/or conditions and then adjust itself to pick a suitable method. In some embodiments, operation 152 is performed by a processor component the same as or similar to information component 31.

At operation 154 of method 150, a trained machine-learning model may be selected based on the obtained configuration, by determining whether the configuration indicates navigation and/or 3D CT scanning. In some embodiments, operation 154 is performed by a processor component the same as or similar to training component 32 or prediction component 34.

At operation 156 of method 150, responsive to the determination that the configuration indicates navigation and 3D CT scanning, a 3D CT scan may be registered with a port and/or camera (e.g., by aligning between a plurality of different coordinate systems and a captured image), and the 3D CT scan corresponding to a region of a patient may be acquired. In some embodiments, operation 156 is performed by a processor component the same as or similar to trajectory component 38 (shown in FIG. 18 and described herein).

At operation 158 of method 150, the image may be captured in real-time.

At operation 160 of method 150, Kambin's triangle may be identified, via the selected model using the acquired 3D CT scan and the captured image. In some embodiments, operation 160 is performed by a processor component the same as or similar to prediction component 34.

Techniques described herein can be implemented in digital electronic circuitry, or in computer hardware, firmware, software, or in combinations of them. The techniques can be implemented as a computer program product, i.e., a computer program tangibly embodied in an information carrier, e.g., in a machine-readable storage device, in machine-readable storage medium, in a computer-readable storage device or, in computer-readable storage medium for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques can be performed by one or more programmable processors executing a computer program to perform functions of the techniques by operating on input data and generating output. Method steps can also be performed by, and apparatus of the techniques can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, such as, magnetic, magneto-optical disks, or optical disks. Information carriers suitable for embodying computer program instructions and data include all forms of non-volatile memory, including by way of example semiconductor memory devices, such as, EPROM, EEPROM, and flash memory devices; magnetic disks, such as, internal hard disks or removable disks; magneto-optical disks; and CD-ROM and DVD-ROM disks. The processor and the memory can be supplemented by, or incorporated in special purpose logic circuitry.

Several embodiments of the disclosure are specifically illustrated and/or described herein. However, it will be appreciated that modifications and variations are contemplated and within the purview of the appended claims.

The disclosure of U.S. Pat. No. 8,518,087 is hereby incorporated by reference in its entirety and should be considered a part of this specification.

What is claimed is:

1. A surgical method, comprising:
acquiring an unsegmented patient scan corresponding to a surgical region or a planned surgical region;
identifying at least one neurological structure in the surgical region or planned surgical region from the unsegmented scan using an image analysis tool that receives as an input the unsegmented scan and outputs a labeled image volume identifying the at least one neurological structure;
creating a patient-specific surgical plan incorporating an approach to a Kambin's triangle that avoids interference with the identified at least one neurological structure;
performing a surgical procedure in accordance with the patient-specific surgical plan; and
displaying the output labeled image volume during the surgical procedure.

2. The surgical method of claim 1, wherein the unsegmented patient scan is a CT or a CBCT scan, and wherein identifying the at least one neurological structure further comprises automatically segmenting the unsegmented scan to identify the at least one neurological structure.

3. The surgical method of claim 1, wherein the image analysis tool uses a deep learning model to automatically segment the at least one neurological structure in the unsegmented patient scan, the method further comprising estimating expected movement of the identified at least one neurological structure based on a change in a position of the patient.

4. The surgical method of claim 3, wherein the change in the position of the patient is from an imaging position to an operating position.

5. The surgical method of claim 3, further comprising adjusting the patient-specific surgical plan in accordance with the expected movement of the at least one neurological structure.

6. The surgical method of claim 1, wherein the unsegmented patient scan is a pre-operative patient scan.

7. A computer-implemented method, comprising:
acquiring a scan corresponding to a region of interest (ROI);
capturing an image of a patient in real-time;
identifying, via a trained machine learning model using (i) the acquired scan and (ii) the captured image, a Kambin's triangle;
overlaying, on the captured image, a representation of the identified Kambin's triangle;
obtaining training data comprising ground truth labeled based on structures identified in (i) previously-taken scans and (ii) corresponding images captured in real-time during a previous medical procedure; and
training the model with the obtained data.

8. The method of claim 7, further comprising:
capturing another image of the patient;
re-identifying, via the trained machine learning model using (i) the acquired scan and (ii) the another captured image, the Kambin's triangle;
updating a confidence criterion associated with the re-identified Kambin's triangle; and
overlaying an updated representation of the re-identified Kambin's triangle on the other captured image.

9. The method of claim 7, further comprising:
selecting, from among (i) vertebral bodies and foramen, (ii) nerve roots, and (iii) bony landmarks, structures in the ROI;
identifying, via the trained machine learning model using (i) the acquired scan and (ii) the captured image, the selected structures each satisfying a confidence criterion, wherein the identification of the Kambin's triangle is based on a relative location of the selected structures; and
overlaying, via a user interface on one or more captured images, a representation of each of the selected structures.

10. The method of claim 7, wherein the machine learning model is a convolutional neural network.

11. The method of claim 7, further comprising:
determining a current distance from a device that captured the image to the identified Kambin's triangle.

12. The method of claim 9, wherein the nerve roots are identified using a corresponding MRI scan, the model being further trained with training data comprising ground truth labeled based on nerve root structures identified in a plurality of previously-taken, MRI scans.

13. The method of claim 7, further comprising:
minimally-invasively advancing an implant or at least a portion of an instrument toward the identified Kambin's triangle, wherein the implant or at least a portion of the instrument has a port and/or a camera;
determining whether a trajectory of the advancement satisfies a criterion; and
adjusting the trajectory such that the criterion is satisfied, in response to the determination that the trajectory did not satisfy the criterion.

14. The method of claim 7, wherein the acquired scan comprises a three-dimensional (3D) computed tomography (CT) scan.

15. The method of claim 13, further comprising:
upon a registration, navigating the instrument or implant, wherein the registration of the scan with a port and/or camera is performed by aligning between a plurality of different coordinate systems of the scan and the captured image.

16. The method of claim 7, further comprising:
determining a position of a dilator advancing towards the identified Kambin's triangle, wherein the image is captured via at least one of a camera, charge coupled device (CCD), and optical sensor mounted on a side of the dilator.

17. The method of claim 9, wherein the representation visually distinguishes the identified Kambin's triangle by encoding the confidence criterion of the selected structures with a color and/or symbol.

18. A method for a situationally aware medical procedure, the method comprising:
- obtaining a configuration of an operating room;
- selecting a trained machine learning model based on the obtained configuration, the selection being performed by determining whether the configuration indicates navigation and 3D CT scanning;
- responsive to the determination that the configuration indicates navigation and 3D CT scanning, (i) registering a 3D CT scan with a port and/or camera, by aligning between a plurality of different coordinate systems of the scan and a captured image of a patient, and (ii) acquiring the 3D CT scan corresponding to a region of the patient;
- capturing in real-time the captured image; and
- identifying, via the selected model using (i) the acquired 3D CT scan and (ii) the captured image, a Kambin's triangle.

19. The method of claim 18, further comprising:
- obtaining, via a user interface, a selection configured to cause display of a representation of the identified Kambin's triangle; and
- obtaining, via a user interface, a selection configured to cause multi-spectral imaging for the capturing of the image.

* * * * *